United States Patent [19]

Eppstein et al.

[11] Patent Number: 5,792,049
[45] Date of Patent: Aug. 11, 1998

[54] SPECTROSCOPIC SYSTEM WITH DISPOSABLE CALIBRATION DEVICE

[75] Inventors: Jonathan A. Eppstein, Atlanta; Mark A. Samuels, Norcross; Keith D. Ignotz, Duluth; Gregory J. Newman, Atlanta, all of Ga.

[73] Assignee: SpectRx, Inc., Norcross, Ga.

[21] Appl. No.: 906,969

[22] Filed: Aug. 6, 1997

Related U.S. Application Data

[63] Continuation of Ser. No. 621,182, Mar. 21, 1996, abandoned, which is a continuation-in-part of Ser. No. 587,949, Jan. 17, 1996.

[51] Int. Cl.$^6$ .................................................. A61B 5/00
[52] U.S. Cl. .................................................. 600/306
[58] Field of Search ................. 128/660.06, 660.07, 128/632, 633, 664, 665; 178/18; 250/491.1; 73/620, 621; 367/140; 378/18, 207; 355/20, 81; 356/243, 244; 600/442, 443, 306, 309, 310, 473, 476

[56] References Cited

U.S. PATENT DOCUMENTS

| | | |
|---|---|---|
| 4,177,798 | 12/1979 | Leveque et al. . |
| 4,241,738 | 12/1980 | Lubbers et al. . |
| 4,267,844 | 5/1981 | Yamanishi ............... 128/633 |
| 4,344,438 | 8/1982 | Schultz . |
| 4,360,270 | 11/1982 | Jeck ............... 356/243 |
| 4,423,736 | 1/1984 | DeWitt et al. . |
| 4,768,516 | 9/1988 | Stoddart et al. . |
| 4,867,557 | 9/1989 | Takatani et al. . |
| 4,894,547 | 1/1990 | Lefell et al. . |
| 5,119,819 | 6/1992 | Thomas et al. . |
| 5,146,091 | 9/1992 | Knudson . |
| 5,349,961 | 9/1994 | Stoddart et al. . |
| 5,355,880 | 10/1994 | Thomas et al. . |
| 5,360,004 | 11/1994 | Purdy et al. . |
| 5,383,452 | 1/1995 | Buchert . |
| 5,435,309 | 7/1995 | Thomas et al. . |
| 5,458,140 | 10/1995 | Eppstein et al. . |

FOREIGN PATENT DOCUMENTS

| 727 002A1 | 11/1996 | European Pat. Off. ......... A61B 5/00 |
|---|---|---|
| 747 002 A1 | 11/1996 | European Pat. Off. ......... A61B 5/00 |

*Primary Examiner*—George Manuel
*Attorney, Agent, or Firm*—Fleshner & Kim

[57] ABSTRACT

A disposable calibration device is used to calibrate a spectroscopic measurement system which transmits radiation to a material or tissue in order to effect measurements such as bilirubin measurements. The disposable calibration device includes a structure with a window through which radiation can be transmitted, as well as a removable calibration target arranged on the window and capable of returning a portion of the radiation for calibrating the spectrometer system. The removable calibration target can be peeled of the window to allow a measurement to be made on the material or tissue. Once a measurement is complete, the disposable calibration device can be discarded and a new calibration device can be inserted on the spectroscopic system.

34 Claims, 20 Drawing Sheets

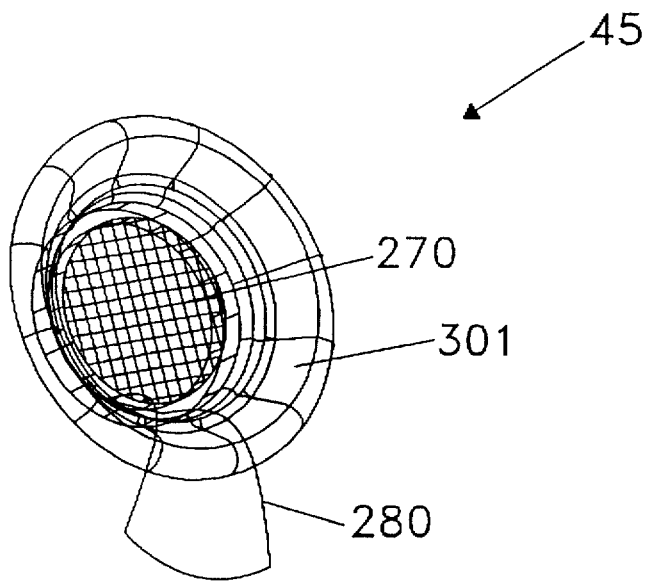
Figure 5A
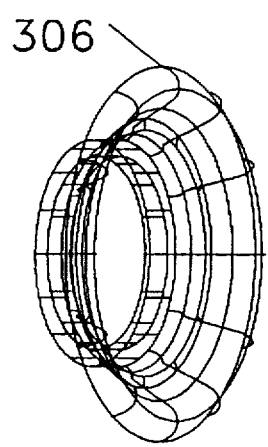 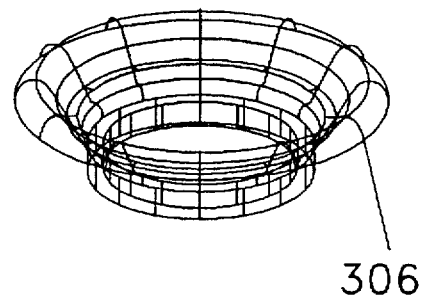
Figure 5B  Figure 5C

SPECTROSCOPIC SYSTEM WITH DISPOSABLE CALIBRATION DEVICE

RELATED APPLICATIONS

This application is a continuation of application Ser. No. 08/621,182 filed Mar. 21, 1996, now abandoned which in turn is a continuation-in-part of application Ser. No. 08/587, 949, entitled "APPARATUS AND METHOD FOR CALIBRATING MEASUREMENT SYSTEM", filed Jan. 17, 1996, the contents of which are hereby incorporated by reference.

BACKGROUND OF THE INVENTION

1. Field of the Invention

This invention relates to spectroscopic instruments requiring calibration to make measurements on animal tissues or other materials, and in particular, to spectroscopic instruments incorporating a disposable calibration target that ensures proper calibration of the spectroscopic instrument, and prevents scratching of optically sensitive windows through which measurements are taken. Once used, the calibration target cannot be reused, thereby helping to control the spread of infection in tissues or helping to control contamination of materials.

More generally, this invention relates to a method and device for calibrating many different types of measurement instruments, and in particular, to a disposable calibration device and method which uses that device for calibrating measurement instruments that perform measurements on a material or tissue. The calibration device includes a calibration target that ensures proper calibration of the measurement instrument, prevents scratching of windows through which measurements are taken, and also prevents reuse of the disposable calibration target, thereby helping to control the spread of infection if the measurements are made on tissues, and helping to prevent contamination if the measurements are made on materials.

2. Background of the Related Art

Spectroscopy is currently used for a wide variety of purposes including to evaluate in-vivo or in-vitro tissue samples. One type of spectroscopy, reflectance spectroscopy, involves diffusely reflecting light from tissue non-invasively. Such spectroscopic measurements must be calibrated prior to use, especially when made for medical or other critical applications. Instrument calibration can be affected by variations in light source intensity, spectral characteristics, lens-aging, lens cleanliness, temperature, detector sensitivity changes, and electronic drift.

Many current instruments provide for a calibration to be performed on a routine basis in order to compensate for these changes in the instrument performance and response. Those calibration methods typically involve measuring the response of a test target with characteristics that remain stable with time and over a range of temperatures. Those methods can also be used to compensate for instrument to instrument variations and any changes that an individual instrument may experience over its working lifetime.

Typically, spectral transmittance, fluorescence (normal and time resolved) and Raman spectroscopy are used to evaluate biological tissues and other materials in order to determine the materials present and measure their concentrations. These methods are also affected by the scattering, reflecting, absorbing and transmitting properties of the instrument's optics, detectors, sources and the media under examination. This is due to the fact that the amount of light reaching the tissue to be measured is a function of those parameters, and in the case of fluorescence and Raman emissions, reabsorption of emission spectra.

Although others have proposed calibration fixtures that compensate for these variations in instrument performance, none have provided a simultaneous solution to both the calibration issue and the problems associated with the spread of infection in a medical setting. Furthermore, calibration standards that are designed to be reused can become damaged by sunlight, temperature, humidity and other effects which could lead to errors in calibration.

Bilirubin

The above spectroscopic instruments can perform a variety of biological measurements. One such application of spectroscopic systems involves detection of bilirubin. Bilirubin is produced from the breakdown of hemoglobin in red blood cells. Under normal conditions the bilirubin is conjugated by glucoronyl transferase, an enzyme present in the liver, and then excreted through the biliary system.

Newborn infants and prematurely born infants are particularly susceptible to hyperbilirubinemia. Hyperbilirubinemia describes the state where there is excessive bilirubin in the body. Often this is due to the lack of functioning glucoronyl transferase enzyme in their liver, or excessive red blood cell breakdown associated with erythroblastosis fetalis.

One method for bilirubin testing include blood based lab assay testing. The "heel stick" blood lab assay is currently the only accepted methodology for quantitative bilirubin testing results in the United States. Of course, this invasive approach requires that the drawing of blood to perform the test.

Non-invasive measurements of the bilirubin concentration in the skin would eliminate the need to draw blood samples from patients for bilirubin analysis. It also provides easy patient interface. Bilirubin can be measured in the aqueous of the eye based on the fluorescent signature. Bilirubin can also be directly measured in the scelera (white) of the eye based on the fluorescent signature. Reflectance measurements can also be made on the tympanic membrane of the ear. Finally, reflectance/scattering based measurements can be made on the skin.

Many attempts have been made to measure cutaneous bilirubin non-invasively. This is because bilirubin from the blood stains the skin as well as other tissues of the body—Jaundice refers to the condition when the bilirubin is visible in the skin and sclera. These attempts include the development of visual reference standards, and transcutaneous reflectance spectroscopy. The absorption spectra of bilirubin, oxidized blood, and melanin, the dominant absorbers in the skin. The concentration of these pigments have distinct absorption spectra. Reflectance bilirubinometers have obtained reasonable correlations between bilirubin levels determined transcutaneously and serum bilirubin concentrations in homogeneous patient populations, but have failed to give satisfactory correlations when used over a heterogeneous population. Since patient populations are rarely homogeneous, transcutaneous bilirubin level measurement has not been widely accepted clinically.

One system which implements a non-invasive cutaneous testing approach for bilirubin and is in wide use in Japan, is the Minolta Jaundice Meter. That approach, however, has not been approved for use in the United States, but is nevertheless, used for screening purposes in some United States institutions. In addition, that approach does not account for variations in skin color and thickness.

Another approach to testing for bilirubin that does not require the drawing of blood is a breath analysis approach introduced by a group from Stanford. This approach does not have the quantitative accuracy required to give a high correlation with serum bilirubin. Hence, it appears to only have potential use as a screening technique.

General Measurement Systems

More generally, there has been an increase in the use of light as a diagnostic tool in many areas of medicine. This development has become more pervasive with the development of appropriate and inexpensive light sources, detection devices and optical fibers that allow for minimal invasiveness.

Moreover, there are many types of measurement systems that require calibrations to be performed on a routine basis in order to compensate for changes in instrument performance and response. This is true for both radiation based measurement systems, i.e., systems that send electromagnetic radiation to the tissue or material to be measured and then detect the return radiation, and acoustic based measurement systems, i.e., systems that send acoustic waves or energy to the tissue or material to be measured and then detect the return acoustic signal. The calibration techniques in both cases typically involve measuring the response of a test target with characteristics that remain stable with time and over a range of temperatures. Those techniques can also be used to compensate for instrument to instrument variations and any changes that an individual instrument may experience over its working lifetime. Often such measurement systems must be periodically calibrated and sometimes must be calibrated prior to each and every use. This calibration becomes especially important when measurements are made for medical or other critical applications.

Radiation measuring systems such as the spectrometer system discussed above, are currently used for a wide variety of purposes including to evaluate tissue or materials. These measuring systems require calibration for a variety of reasons including variations in the radiation source intensity, changes in spectral characteristics of the tissue or material, component aging and cleanliness, changes in temperature, radiation detector sensitivity changes, and electronic drifting.

Examples of radiation type measurement systems that often require some type of calibration include in addition to spectrometers, instruments such as laser radar, radar or any other radiation measuring instrument that outputs radiation to a tissue or material and then measures some aspect of the return signal.

Acoustic type measuring systems are also used for a wide variety of purposes including to evaluate tissue or materials. Often these measurement systems must also be periodically calibrated and sometimes must be calibrated prior to each use. Acoustic measurement systems also require calibration for a variety of reasons including variations in the output energy of the acoustic wave source, changes in spectral characteristics of the tissue or material, changes in temperature, detector sensitivity changes, and electronic drift.

Examples of acoustic type measurement systems that often require some type of calibration include acoustic spectrometers, and interferometers or any other system which uses an acoustic wave measuring instrument that outputs acoustic energy to a material and then measures some portion of the return signal.

Various types of calibration techniques and devices have been attempted. For example, U.S. Pat. No. 5,365,925 describes a calibration boot which includes a plurality of materials, which is placed over an optical catheter for the purpose of making a multipoint calibration of reflected or backscattered light. U.S. Pat. No. 5,311,273 describes a method of using four black body radiators to provide calibration of an infrared spectrometer. However, neither of these approaches involves an inexpensive calibration target that can be easily discarded after each use, and thus does not prevent a user from taking a measurement without going through a calibration step.

U.S. Pat. No. 4,981,355 describes a calibration device for the in vitro calibration of a light guide, whereby a polyethylene material has a plurality of light scattering particles and a plurality of light absorbing particles which yields a neutral density filtering type of effect, uniformly distributing light in the plastic parts of the calibrator. The calibrator can be positioned into a sterile tray which is protected by tear off plastic. Once the calibration is complete, the surgeon removes the catheter from the calibrator and the tray in which it is held and then presumably disposes of the calibration device and its tray. This approach, however, is neither simple nor inexpensive.

U.S. Pat. No. 4,796,633 describes a calibration reference apparatus that fits over a light guide. A stop limits the extent to which the light guide can be advanced into the cavity whereby an endface of the light guide is spaced from a region of the surface to define a gap. The end wall and the gap are adapted to return a known ratio of the light directed into the gap from the end face of the light guide. Again, however, this approach does not involve an inexpensive, disposable calibration device.

U.S. Pat. No. 4,744,656 discloses a calibration boot that snaps into place over an optical catheter allowing calibration of the catheter before use. Once the calibration is complete, the boot is removed and the optical catheter is ready for use. Each new catheter comes with a new boot. However, the boot is not present during the measurement and there is no provision to prevent reuse of the boot.

SUMMARY OF THE INVENTION

An object, therefore, of the invention is to provide an optical system which utilizes an optical instrument with a calibration device.

Another object of the invention is to provide an spectroscopic system which utilizes a spectrometer as the optical instrument and a disposable calibration device.

Another object of the invention is to provide a spectroscopic system that utilizes a calibration device which can be inexpensively mass produced.

Another object of the invention is to provide a spectroscopic system which utilizes a disposable calibration device that helps prevent infection of tissue to be measured.

Another object of the invention is to provide a spectroscopic system which uses a calibration device which provides an optically clear, scratch-free window between the optical instrument and the tissue or material to be measured.

Another object of the invention is to provide a spectrometer system with a calibration device that serves to compensate for the effects of variations from one spectrometer system to the next.

Another object of the invention is to provide a spectrometer system with a calibration device that serves to compensate for changes over time in properties of the spectrometer instrument in the spectrometer system.

Another object of the invention is to provide a spectrometer system with a calibration device that serves to compensate for changes over a wide range of temperatures in properties of an individual optical instrument.

One advantage of the spectrometer system is that once used, the calibration device cannot be re-used, thereby ensuring against infection from one person to another person in that the calibration device is discarded after a measurement is performed.

An advantage of the calibration device in general is that it can be used in radiation type measurement systems.

Another advantage of the calibration device in general is that it can be used in acoustic type measurement systems.

Another general advantage of the calibration device is that it helps reduce the possibility of contamination from one material to another material.

One feature of the invention is that it can utilize an optical instrument operating in the ultra-violet, visible and/or the infrared regimes.

Another feature of the invention is that it can utilize a spectrometer as the optical instrument according to one embodiment of the invention.

Another feature of the invention is that it utilizes a disposable calibration device that can include material that has a stable or predictable spectroscopic signature.

Another feature of the invention is that it utilizes a disposable calibration device with a window through which radiation can be transmitted to tissue or material to be measured.

Another feature of the invention is that it utilizes a calibration target that can be peeled away from the window.

Another feature of the invention is that the calibration target can have a tear tab which allows the calibration target to be easily handled without disturbing the window or calibration target in contact with the window.

Another feature of the invention is that the calibration target can be attached to the window by a static cling brought about by a proper selection of materials for the window and the calibration target.

Another feature of the invention is that the calibration device can include a structure which can be cone-shaped.

Another feature of the invention is that the cone-shaped structure has a proximal end that attaches to the optical instrument with which it is used.

Another feature of the invention is that the calibration device can include an outer annulus which comes into contact with the tissue or material to be measured.

Another feature of the invention is that the calibration device can include a landing annulus which aids in arranging the window on the tissue or material for taking a measurement.

These and other objects, advantages and features are accomplished by the provision of a spectrometer system, comprising: a spectrometer instrument which transmits radiation to a material or tissue in order to effect measurements; a calibration device holder; a calibration device which can be arranged in said calibration device holder, said calibration device, comprising: a structure including a window through which the radiation can be transmitted; and a removable calibration target arranged on said window and capable of returning a portion of said radiation for calibrating the spectrometer instrument, whereby the removable calibration target can be removed from said window to allow a measurement to be made on the material or tissue.

In one approach, the window in the spectrometer system can include material through which said radiation can pass, and the removable calibration target includes a tear tab which can be gripped to remove said removable calibration target from said window.

The structure and window can comprise a barrier or infection shield between the material or tissue and the spectrometer system.

The spectrometer instrument in the spectrometer system can include: an optical unit for outputting output radiation and for receiving received radiation and detecting said received radiation as spectral return information; and a processor coupled to said optical unit for receiving and processing said spectral return information.

These and other objects, advantages and features are accomplished by the provision of a spectrometer system, comprising: a spectrometer instrument which transmits radiation to a material or tissue in order to effect measurements; a calibration device holder; a calibration device which can be arranged on said calibration device holder, said calibration device, comprising: a structure through which the radiation can be transmitted; and a removable calibration target arranged about said structure and capable of returning a portion of said radiation for calibrating the spectrometer instrument, whereby the removable calibration target can be removed from said structure to allow a measurement to be made on the material or tissue.

These and other objects, advantages and features are accomplished by the provision of a method for transcutaneous determination of bilirubin concentration in tissue, including the steps of: performing a calibration measurement on a calibration target and storing resulting calibration data; illuminating said tissue with light; detecting a frequency spectrum of light reflected from said tissue; calculating, from a first portion of said spectrum, a first parameter indicative of a maturity of said tissue; calculating, from a second portion of said spectrum, a second parameter indicative of an amount of melanin in said tissue; calculating, from a third portion of said spectrum, a third parameter indicative of a blood content of said tissue; calculating, from a fourth portion of said spectrum, a fourth parameter indicative of an uncorrected bilirubin concentration in said tissue; calculating a corrected bilirubin concentration in said tissue as a function of said first, second, third, and fourth parameters; adjusting said corrected bilirubin concentration using said resulting calibration data to yield a calibrated and corrected bilirubin concentration, whereby said calibrated and corrected bilirubin concentration compensates for unit to unit and time varying changes in source luminosity, delivery optics, collection optics, detection sensitivity, electronic drift, and environmental conditions such as temperature and humidity.

These and other objects, advantages and features are accomplished by the provision of a spectrometer system, comprising: a housing including a calibration device holder; a spectrometer instrument arranged in said housing, said spectrometer instrument transmitting radiation through said calibration device holder to a material or tissue in order to effect measurements; and a calibration device which can be attached to said calibration device holder, said calibration device, comprising: a structure including a window through which the radiation can be transmitted; and a removable calibration target arranged on said window and capable of returning a portion of said radiation for calibrating the spectrometer instrument, whereby the removable calibration target can be removed from said window to allow a measurement to be made on the material or tissue.

The optical unit of the spectrometer system can further comprises a grating for diffracting said return radiation according to wavelengths therein toward said detector array.

7

These and other objects, advantages and features are accomplished by the provision of a method for calibrating a spectrometer system that outputs radiation from an output end, comprising: placing a calibrating device over the output end of the spectrometer system, wherein the calibration device has a removable calibration target; activating the spectrometer system to perform a calibration measurement; and removing the removable calibration target from the calibration device.

The removing step can include removing the removable calibration target from the calibration device while leaving a window attached to the spectrometer system, and said radiation is output through that window.

These and other objects, advantages and features will become more apparent from the following description of embodiments thereof taken in conjunction with the accompanying drawings.

BRIEF DESCRIPTION OF THE DRAWINGS

FIGS. 5A, 5B, and 5C show three more perspective views of the calibration device, where FIGS. 5B and 5C show the calibration target removed.

8

DETAILED DESCRIPTION OF PREFERRED EMBODIMENTS

A spectrometer system according to one embodiment of the invention will be presented that uses a disposable calibration device for calibration. First, however, FIGS. 1A through 7B discuss a general calibration device which can be used in any type of measurement system—be it an acoustic type measurement system or a radiation type measurement system.

Figure 1A:
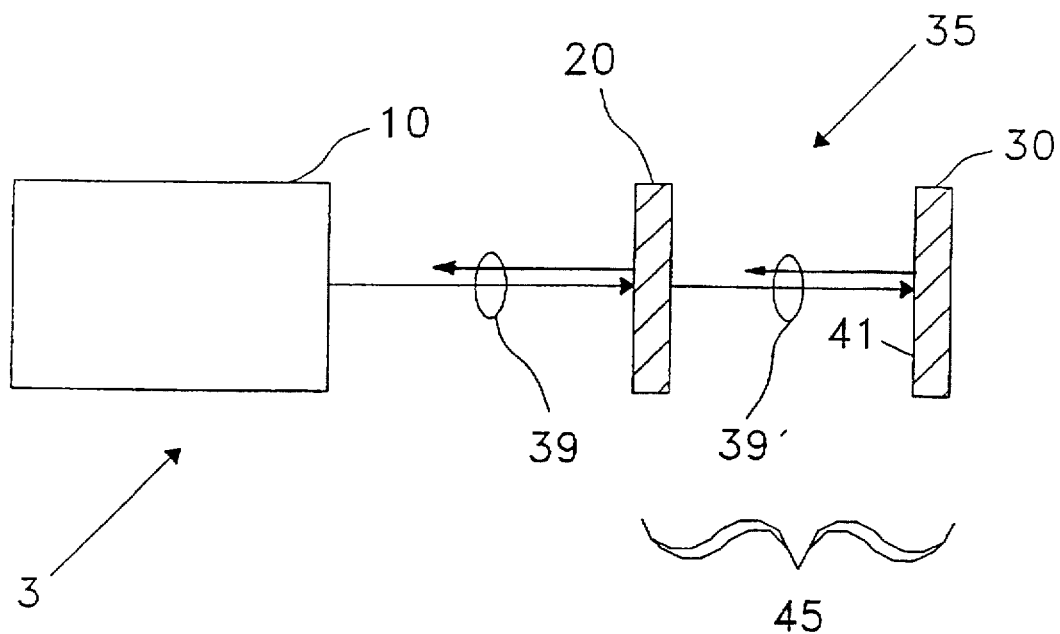
FIG. 1A shows a schematic view of a measurement system in a calibration mode.

FIG. 1A is a schematic view of a system 3 in a calibration mode. System 3 includes an instrument 10 which transmits electro-magnetic radiation 39. Alternatively, instrument 10 can be an instrument which transmits acoustic waves. Reference number 39 will be used to represent electro-magnetic radiation or acoustic radiation just as reference number 10 will be used to represent an instrument that outputs either electro-magnetic radiation 39 or acoustic waves 39. If instrument 10 outputs electromagnetic radiation 39, that radiation can lie within the visible, infrared, ultra-violet regimes, and/or within the rf, microwave and millimeter wave regimes. With regard to electromagnetic radiation 39, instrument 10 can be a spectrometer, laser radar, radar or any other radiation measuring instrument that outputs radiation to a material 40 and then measures some portion of the return signal. With regard to acousto-optic waves 39, instrument 10 can be an acoustic measuring/imaging device that outputs acoustic waves and measures the return acoustic wave signal. The discussion that follows is drawn to electromagnetic radiation 39, it being understood that an analogous discussion applies for the case in which acoustic waves are output from instrument 10. Radiation 39 is transmitted toward and through shield 20 toward a calibration target 30. Shield 20 serves as a barrier between instrument 10 and material or tissue 40 to be measured and hence functions to reduce contamination of material or tissue 40. One major (but not the only) purpose of shield 20 is to guard against possible infection when living tissue 40 is measured. Hence, shield 20 might also be referred to as an infection shield.

Shield 20 must be at least partially transmissive to radiation 39 such that a portion thereof appears as radiation 39'. Radiation 39' passes through region 35 and reaches surface 41 of calibration target 30. Surface 41 can be the same material as calibration target 30 or a specially applied layer. Surface 41 reflects or scatters radiation back. Note that throughout this specification, reflection and scattering are used interchangeably and are meant to indicate that radiation travels back toward instrument 10. Also, region 35 can be a variety adhesives, gels, pastes, or other materials. The combination of shield 20, region 35 and calibration target 30 comprise calibration device 45. Once system 3 with instrument 10 is calibrated, calibration target 30 is removed, and system 3 is now ready to take measurements on material 40 through shield 20.

Figure 1B:
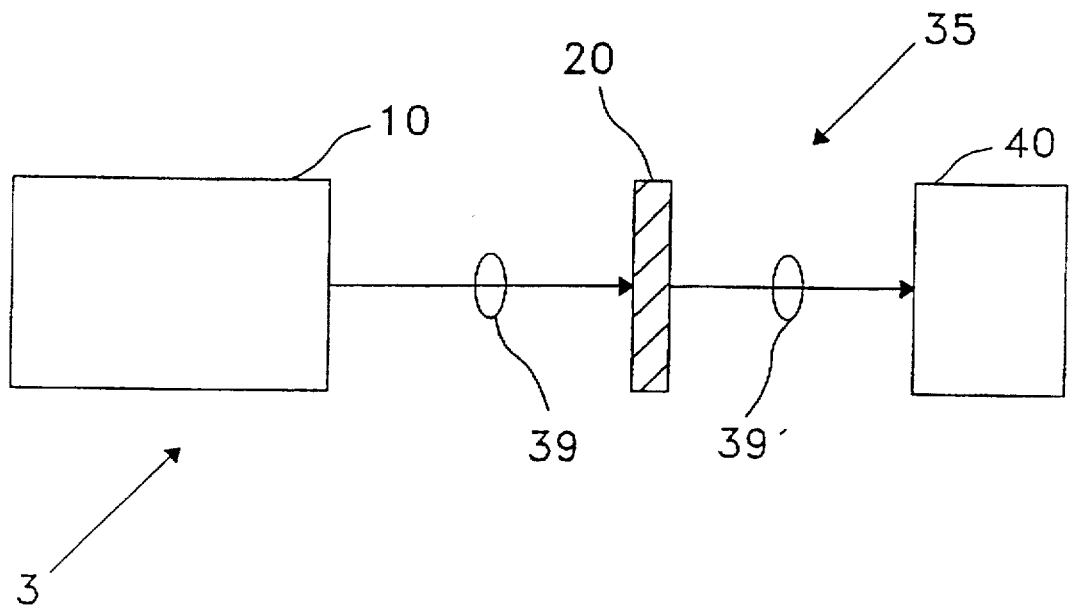
FIG. 1B shows the same system in a measurement mode wherein the calibration target has been removed and radiation is now reaching the tissue or material to be measured.

FIG. 1B shows system 3 in measurement mode in that calibration target 30 has been removed and radiation 39' is now reaching tissue or material 40 to be measured through shield 20.

With regard to electromagnetic radiation 39, instrument 10 can be a spectrometer, laser radar, radar or any other radiation measuring instrument that outputs radiation to a material 40 and then measures some portion of the return signal. With regard to acousto-optic waves 39, instrument 10 can be an acoustic measuring/imaging device that outputs acoustic waves and measures the return acoustic wave signal.

Figure 2A:
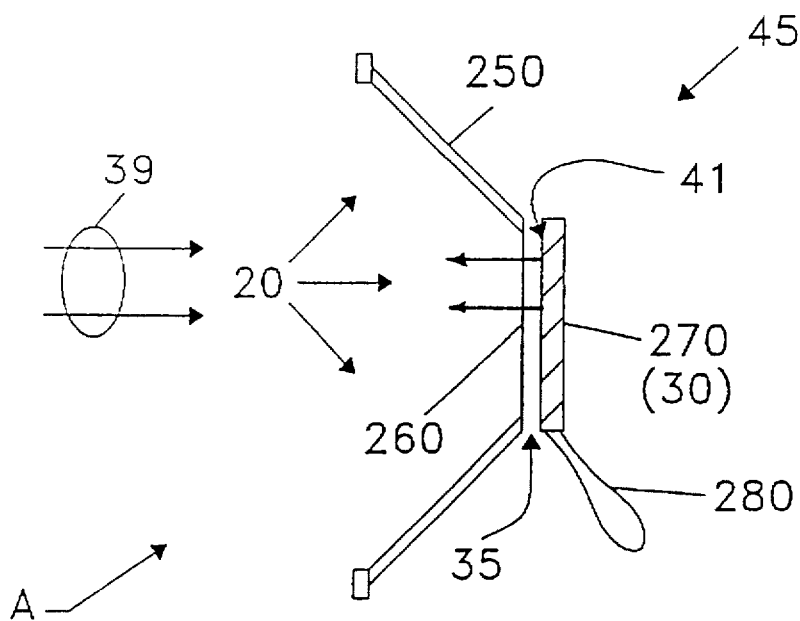
FIG. 2A shows a schematic representation of a preferred embodiment of the calibration device used in the calibration mode.

FIG. 2A shows a schematic representation of a preferred embodiment of device 45 used in the calibration mode for an instrument 10 (not shown). Device 45 includes shield supporting structure 250 with window 260 (structure 250 and window 260 comprising shield 20 from FIG. 1A). In an alternative embodiment, window 260 can simply be an opening and the discussion regarding window 260 should be read to encompass either an opening or a structure where appropriate. Also, in this embodiment, supporting structure 250 has a cone-type shape cut off at top 265 and window 260 is circular shaped and is arranged to cover top 265. It should be understood, however, that the shape of shield structure 250 need not be limited to this cone-type shape and window 260 need not be limited to a circular shape. Finally, device 45 includes calibration target 270 (corresponding to target 30 from FIG. 1A) with tab 280.

Device 45 receives radiation 39 (which will be considered from here on out to be essentially the same as radiation 39' in accordance with a preferred embodiment) from instrument 10 which passes through window 260 and region 35 and then reaches surface 41 of calibration target 270. Window 260 must be at least partially and preferably nearly completely transparent to radiation 39. Region 35 can be an adhesive, gel, liquid and/or free space. A preferred embodiment, however, has window 260 statically charged with respect to surface 41 of calibration target 270, thereby holding calibration target 270 in place. Radiation 39 is then incident on surface 41 of calibration target 270.

Calibration target 270 should be selected to have a known reflection spectrum for calibration purposes (note that radiation is scattered or reflected from 270). For instruments 10 which perform measurements of intensity independent of wavelength, a high reflection surface 41 of calibration target 270 may be advantageous. This might include radar, laser radar and interferometric type instruments. Note however, that such instruments might also benefit from other lower reflecting calibrating surfaces 41 of calibration target 270 as well. Instruments 10 such as spectrometers should use calibration targets that have a well defined or known spectral characteristic.

Figure 2B:
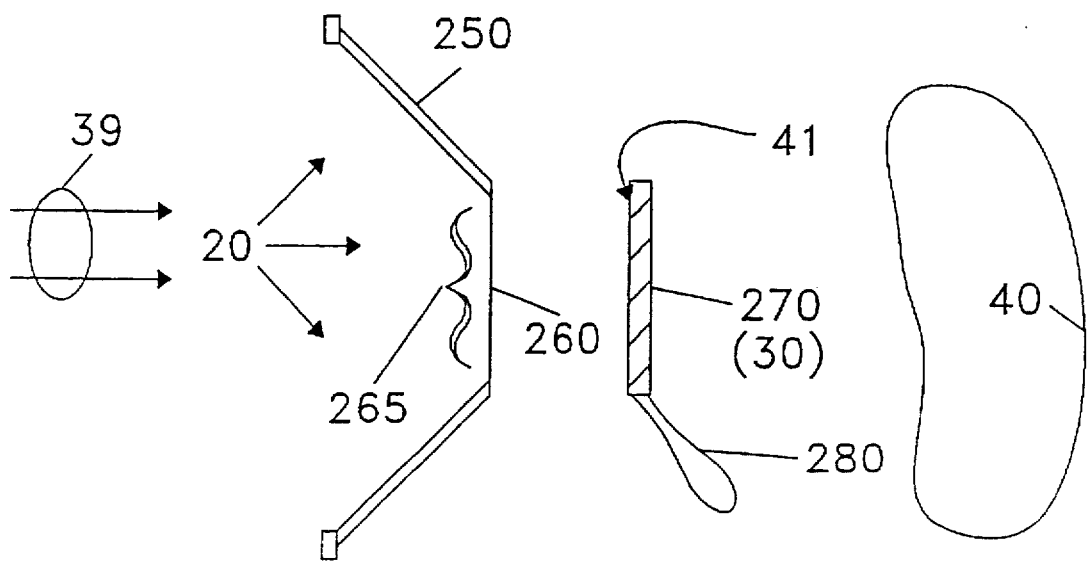
FIG. 2B shows the calibration device after the calibration target is removed (peeled) from the window.

Once system 3 with instrument 10 is calibrated, calibration target 270 is removed (peeled) from window 260 by pulling on a tear tab 280 as shown in FIG. 2B. Tear tab 280 allows the user to remove the calibration target 270 from window 260 of shield 20. System 3 is now ready to take measurements on material 40 through window 260.

Figure 3A:
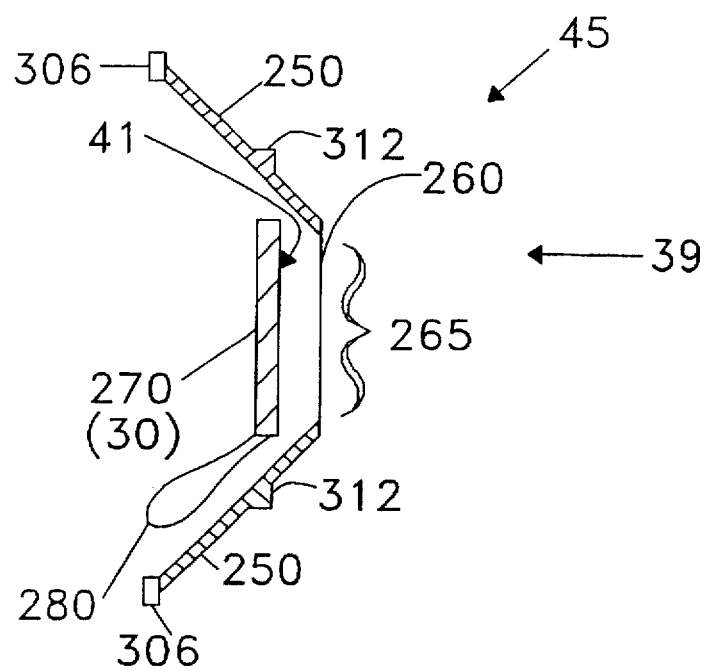
FIGS. 3A and 3B correspond to FIGS. 2A and 2B, but with the radiation entering from the right hand side and the calibration target is attached to the window within the structure.
Figure 3B:
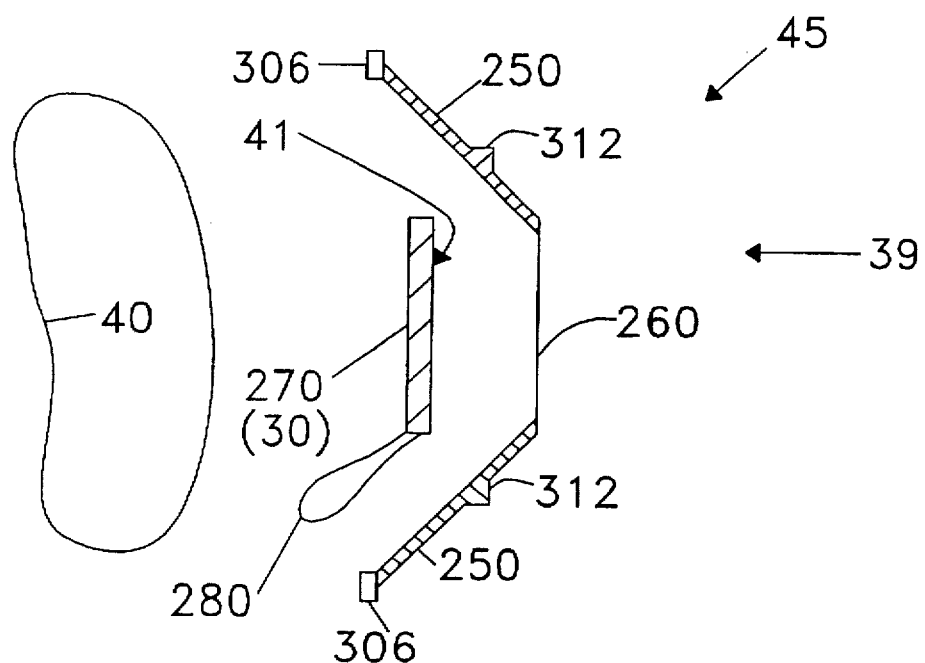

FIGS. 3A and 3B correspond to FIGS. 2A and 2B, but with radiation 39 entering from the right hand side and calibration target 270 attached to window 260 within structure 250. In this case, an outer annular ring 306 comes into contact with tissue or material 40 to be measured. Structure 250 includes an annular ring or ridge 312 which secures device 45 to instrument 10 (not shown).

Referring to FIGS. 3A and 3B, device 45 receives radiation 39 from instrument 10 which passes through window 260 and reaches surface 41 of calibration target 270. Again region 35 can be an adhesive, gel, liquid and/or free space, but a preferred embodiment, has window 260 statically charged with respect to surface 41 of calibration target 270, thereby holding calibration target 270 in place. Radiation 39 passes though window 260 to yield radiation 39' which is preferably identical to radiation 39. Radiation 39' then is incident on surface 41 of calibration target 270.

Once calibration has been completed, calibration target 270 is removed from window 260 using tear tab 280 as shown in FIG. 3B. Outer annular ring 306 is then arranged to contact tissue or material 40 for a measurement.

Figure 3C:
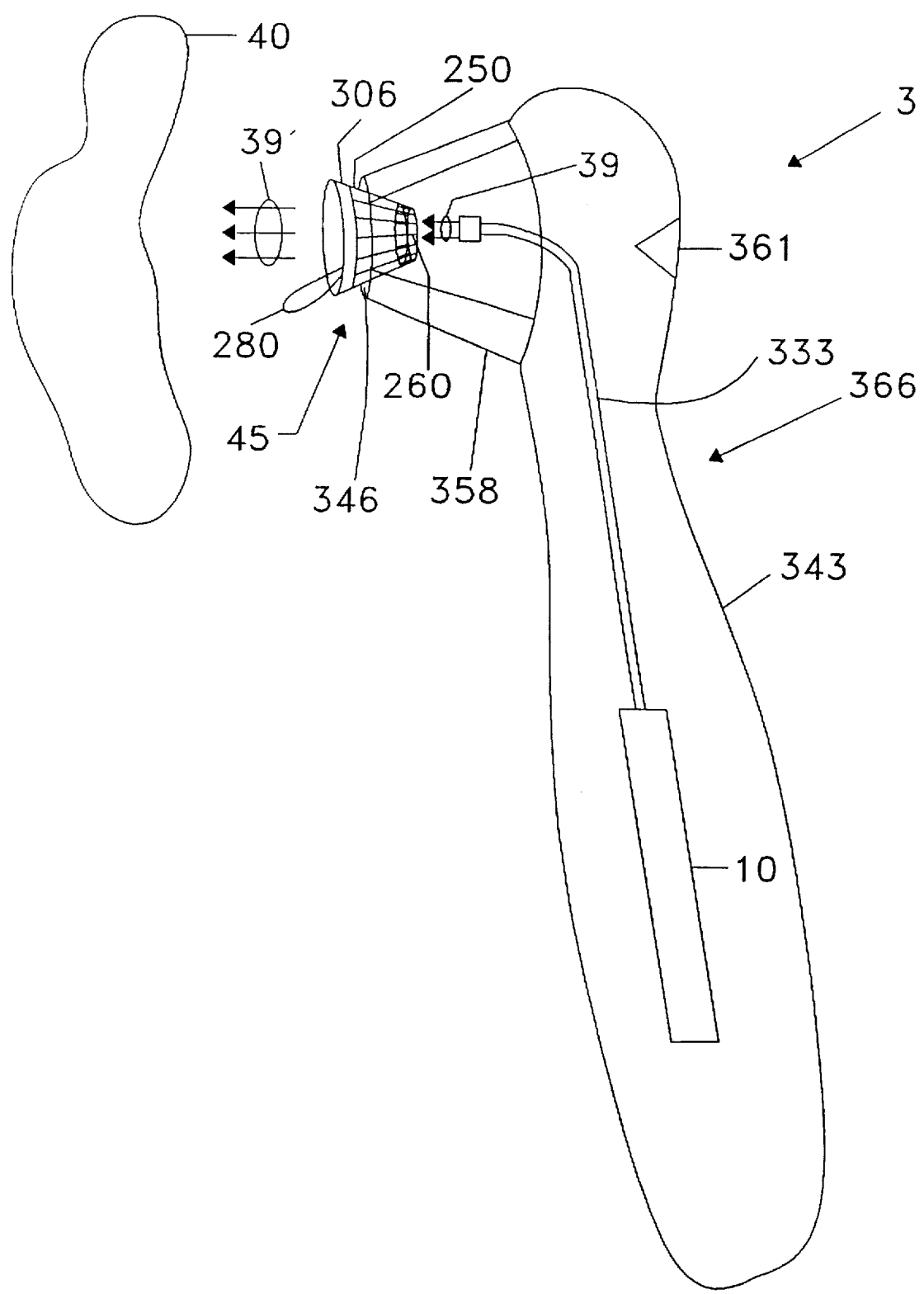
FIG. 3C shows a measurement system which utilizes a disposable calibration device as in FIGS. 3A and 3B.

FIG. 3C shows a measurement system 3 which utilizes a disposable calibration device 45 for instrument 10. Here, instrument 10 is an optical instrument such as a spectrometer and radiation 39 is optical radiation which can be in the visible, uv and/or infrared regions. System 3 includes a housing 343 which is approximately the size of a human hand. Instrument 10 is coupled to calibration device 45 via optical fiber 333. Calibration device 45 is inserted into an opening end 346 of a cone-shaped holder 358 of housing 343. Cone shaped holder 358 can have any shape depending among other things on the shape of calibration device 270 and hence will alternatively be referred to as a calibration device receiving element. Holder 358 can be a separate piece or part of housing 343. It is preferable that holder 358 be capable of receiving calibration device 45, to allow a calibration measurement to be made, but then allowing calibration target 270 to be readily removed for the actual measurement on material or tissue 40, and then allowing calibration device 45 to be removed so that system 3 is again ready to receive a new calibration device 45.

Curved portion 366 of housing 343 allows the hand to comfortably hold system 3. A person can initiate a calibration or measurement as the case may be, by pressing a push button 361 with his or her thumb. Once a calibration measurement has been performed, tear tab 280 can be used to peel calibration target 270 away from window 260 (not shown in this view), and system 3 is now ready to make a measurement on material or tissue 40.

Figure 3D:
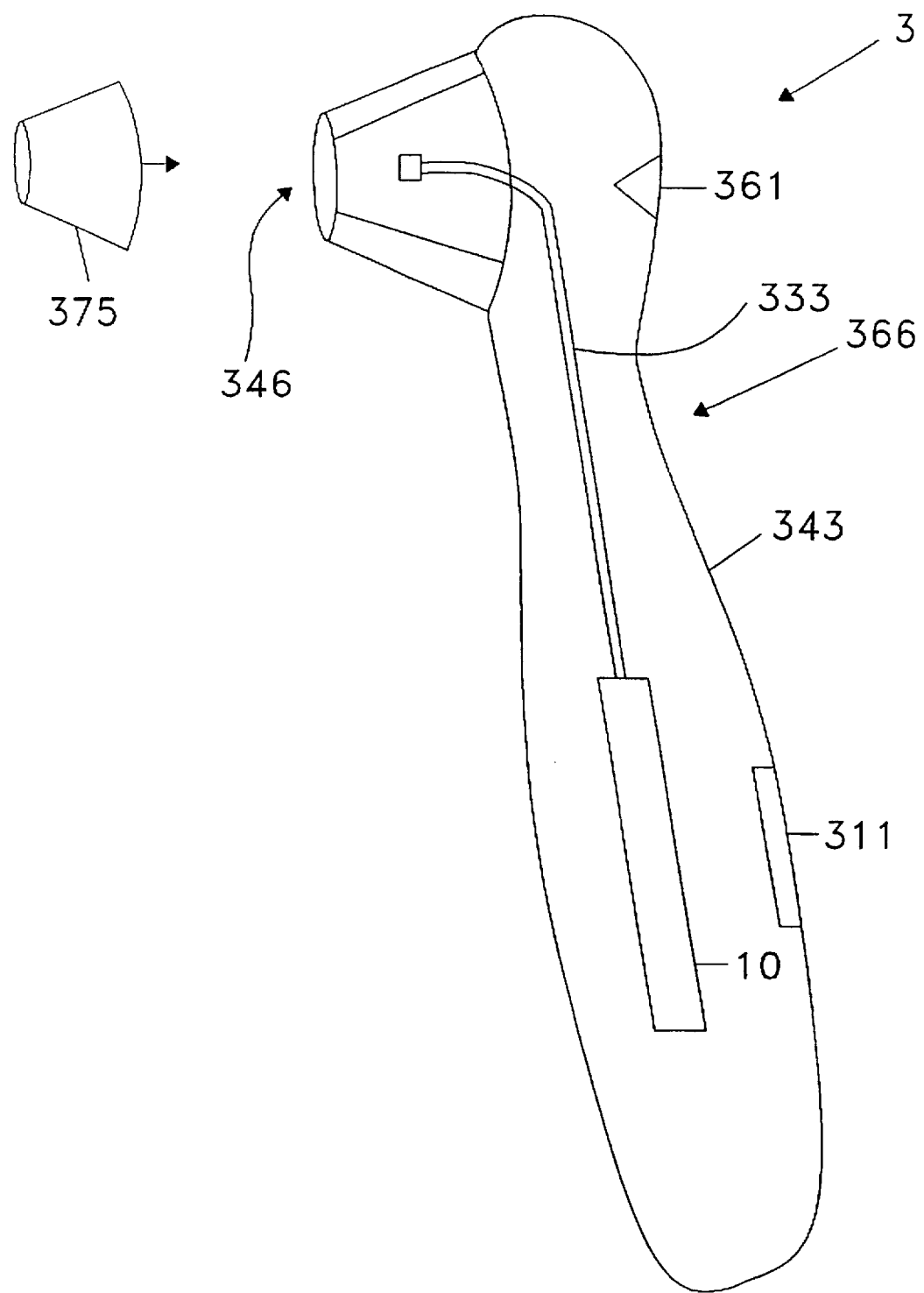
FIG. 3D shows the same measurement system with the calibration device removed.

FIG. 3D shows the same measurement system with calibration device 45 removed. A new calibration device 45 must be inserted into end 346 of system 3 and the above discussed process of calibration must be repeated and calibration target 270 peeled away before system 3 is ready to perform a new measurement. Alternatively, a cap 375 can be placed over end 346 between measurements.

In all of the above embodiments, calibration target 270 can have calibration information fitted directly on surface 41 of calibration target 270, and which can be read by instrument 10. This calibration information can include a message read by instrument 10 which initiates a system shut down after one or a predetermined number of measurements are performed. For the case of shut down upon a single measurement, contamination is avoided, because that system 3 cannot be reused on a new or different material or tissue until a new calibration device 45 replaces the used calibration device. In an alternative approach, this calibration information can be directly input into system 3 by a user using input 311.

Figure 3E:
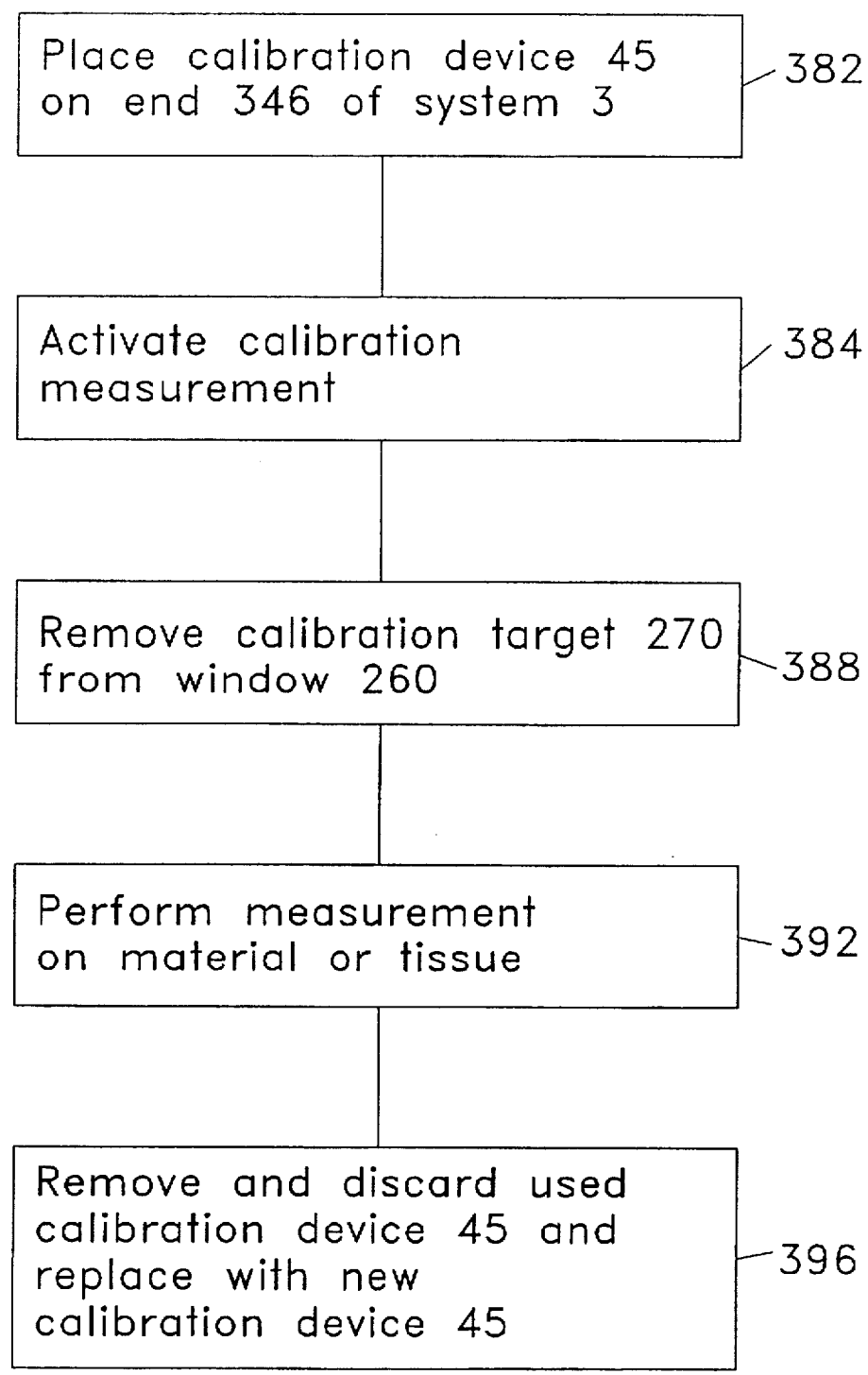
FIG. 3E summarizes the steps involved for calibrating the above measurement system and then taking a measurement on material or tissue.

FIG. 3E summarizes the steps involved for system 3 to take a measurement on material or tissue 40. In particular, step 382 involves placing calibration device 45 on end 346 of system 3. At this point, calibration device 45 still has calibration target 270 covering window 260. A calibration measurement is performed by system 3 at step 384 by pressing push button 361 which activates instrument 10. Step 388 involves removing calibration target 270 from window 260 using tear tab 280. Step 392 then involves performing a measurement on tissue or material 40 to be measured. This might involve a single measurement or multiple measurements (if cross contamination is not an issue) on the same or a similar tissue or material. That is, if measurements are being performed on a person's tissue, several measurements might be repeated in the same vicinity of that person's tissue. Similarly, if measurements are being made on some type of material, multiple measurements can be made in the vicinity of that measurement provided that cross contamination is not an issue. Finally, once the measurement or measurements have been completed, calibration device 45 is removed, discarded, and replaced with a new calibration device 45 at step 396. Alternatively, used calibration device 45 can be removed, discarded, and cap 375 can be placed over end 346 until a new measurement is to be made.

Figure 4A:
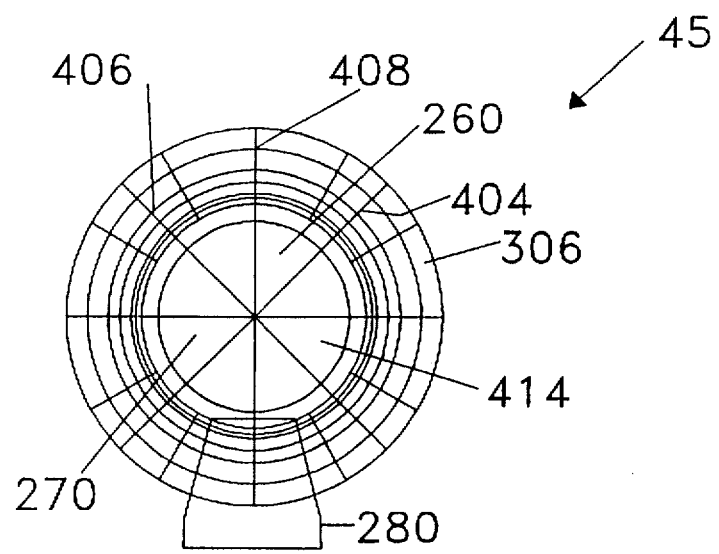
FIGS. 4A and 4B show a top view and a side view, respectively, of a calibration device similar to the calibration device in FIG. 3A.
Figure 4B:
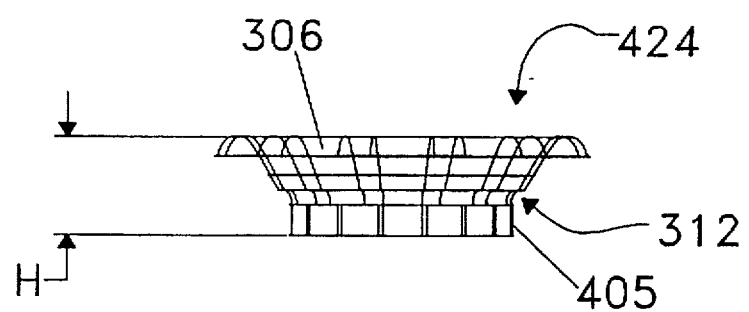
Figure 4C:
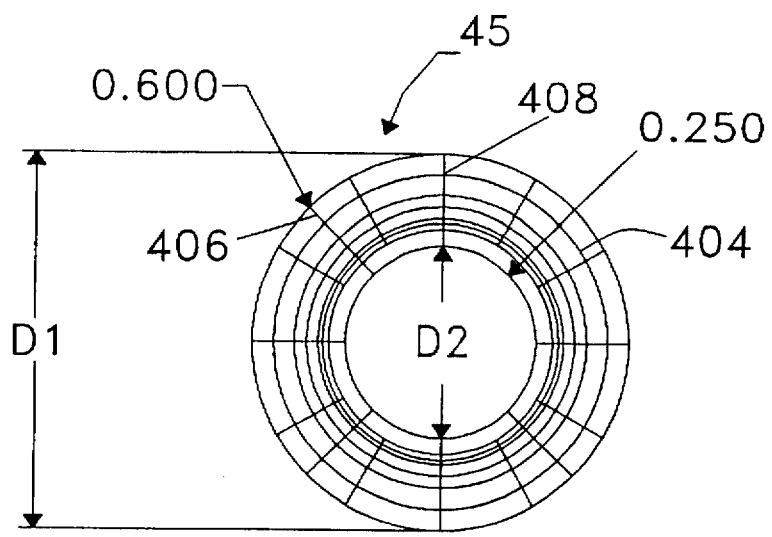
FIGS. 4C and 4D show the same views as FIGS. 4A and 4B, respectively, with the calibration target removed.
Figure 4D:
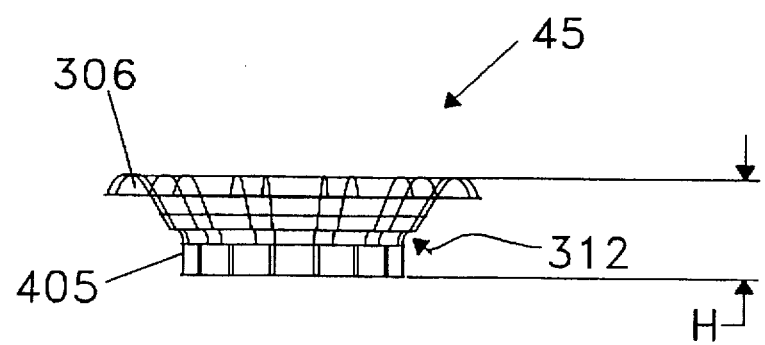

FIGS. 4A and 4B show a top view and a side view, respectively, of calibration device 45 similar, but not identical to device 45. FIGS. 4C and 4D show the same views as FIGS. 4A and 4B, respectively, with calibration target 270 removed. Device 45 can include cross-hatched lines 404, 406, and 408. Lines 404, 406, and 408 can be placed on the backside 414 of calibration target 270 as well as along inner-sides 424 of structure 250 and outer annular ring 306 of calibration target 270 which can aid in the placement of window 260 on material or tissue 40. Cross-hatched lines 404, 406, and 408 are designed to be aligned prior to calibration. Once the calibration measurement is made, calibration target 270 is removed, thereby making system 3 ready to make a calibrated measurement. If a user then tries to reattach calibration target 270, they will note that lines 404, 406 and 408 are no longer properly aligned. Also, surface 41 can be made so that once a calibration measurement is made, calibration target 270 no longer attaches or sticks to window 260. Cross-hatched lines 404, 406 and 408 define six zones (here each zone is shown as a wedge, but the shape can be of any form). Also, note that an additional cross-hatched line is shown which further divides two of the wedges and hence that the number of zones need not be limited to six. Each of the cross-hatched lines are made to appear on both calibration target 270 and window 260. The different zones on calibration target 270 have different reflectivities or different reflectance signatures. The different zones on calibration target 270 are matched up with corresponding zones on windows 260 at the manufacturing stage. The different zones on calibration target 270 thereby create a rotary reflectance signature. In this manner, calibration is only valid if the rotary reflectance signature is duplicated with each measurement. If calibration target 270 is not properly oriented, the calibration would not be valid. This helps to avoid the reuse of device 45.

Figure 4E:
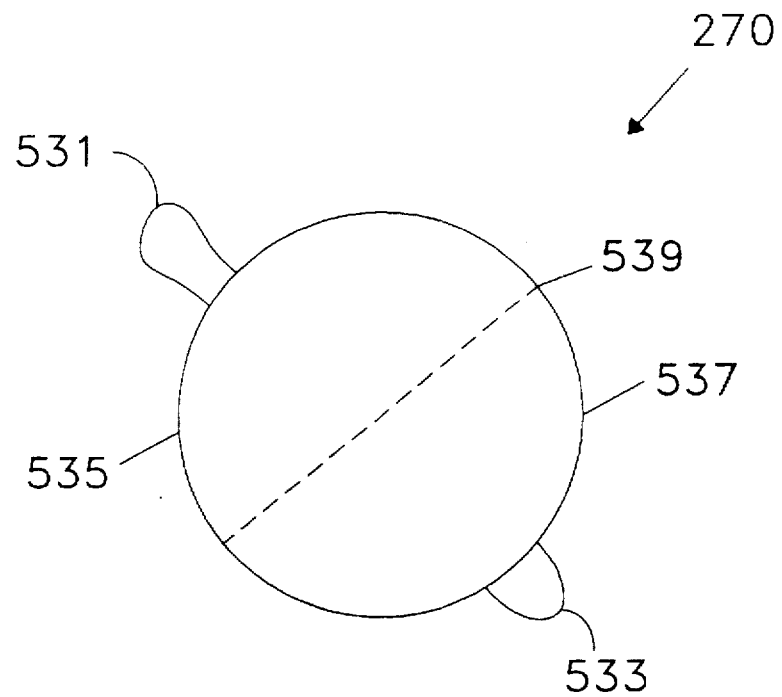
FIG. 4E shows the calibration target with two pull tabs at its sides and a perforation down the middle designed to prevent reuse.

Calibration target 270 can be manufactured with two pull tabs at its sides as shown in FIG. 4E. Here, two pull tabs 531 and 533 are attached to two halves 535 and 537 of target 270. The two halves 535 and 537 have a mechanical perforation 539. When target 270 is pulled away from window 260 (see FIGS. 2A or 2B), it breaks along perforation 539, thereby making it difficult to reuse. The remaining half of target 270 can be pulled away using the remaining tab. Perforation 539 need not be a straight line, but can be curved or spiral shaped. If perforation 539 is a spiral, a single tab (e.g., tab 531) can be used, in which case target 270 is unraveled and peeled away from window 260 either from its perimeter to its center (if the tab is on the perimeter of target 270), or from its center to its perimeter (if the tab is on the center of target 270). The number of revolutions of the perforation spiral can vary from less than one to three or more.

Device 45 in FIGS. 4B and 4D has annular ring 306 which contacts the material or tissue 40 to be measured. Device 45 also has a collar section 405 that attaches to the optical outlet (not shown) of instrument 10. Diameter D1 is defined to be the diameter of annular ring 306 and diameter D2 is defined to be the diameter of window 260, and height H is defined to be the distance from window 260 to annular ring 306.

FIGS. 5A, 5B, and 5C show three more perspective views of device 45 (FIGS. 5B and 5C have calibration target 270 removed).

Figure 6:
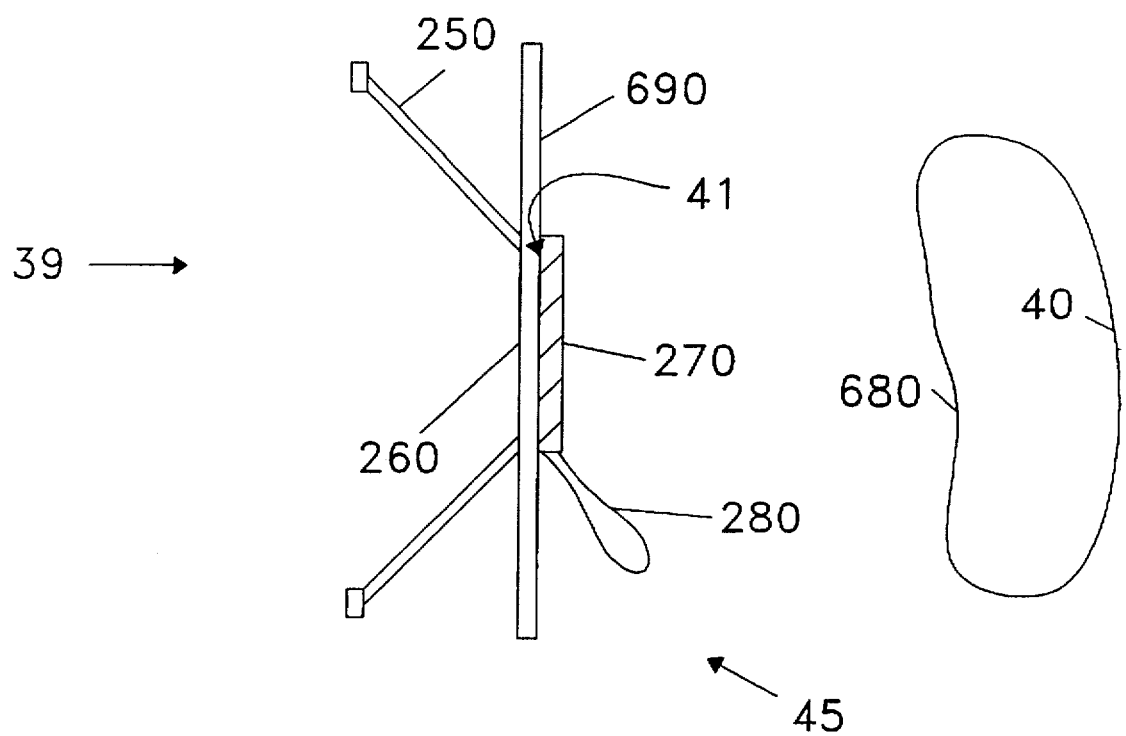
FIG. 6 shows a calibration device according to another embodiment of the invention.

FIG. 6 shows a calibration device 45 according to another embodiment of the invention. Here, a landing annulus 690 is affixed to structure 250. Landing annulus 690 serves to fix the angle at which radiation is incident on surface 680. Landing annulus 690 is preferably transparent to radiation 39. Calibration occurs as before with the presence of calibration target 270. A calibration measurement is taken and then calibration target 270 is removed and annulus 690 remains in place. Device 45 is then placed on surface 680 such that annulus 690 lies flat on surface 680, thereby ensuring that radiation 39 is incident approximately normal to surface 680 as it was to surface 41 of calibration target 270. On the other hand, depending on the type of measurement, it may be preferable due to unwanted spectral reflections, to have radiation 39 incident at an angle off normal to surface 680. Landing annulus 690 can be a separate piece affixed to structure 250 and comprised of any type of rigid material such as various plastics. If infection to surface 680 of tissue 40 is an issue, then landing annulus 690 should be removable from structure 250. Alternatively, annulus 690 can simply be an extension of window 260 itself.

Structure 250 is preferably fabricated from molded plastic with a smooth window zone defined for window 260. Using plastic molding allows structure 250 to be fabricated at low cost and in a wide variety of shapes and sizes. Calibration target 270 can also be fabricated from plastic and may also have a dye or other material added as surface 41 to provide sufficient spectral detail to effect the necessary calibration. Calibration target 270 can be attached to window 260 in such a way that once removed, it cannot be readily re-attached. One implementation is to fabricate calibration target 270 using a statically clinging type plastic, and to fabricate structure 250 using an appropriate material such as an acrylic called polymethyl methacrylate (PMMA) both of which are available from 3M Corporation.

Figure 7A:
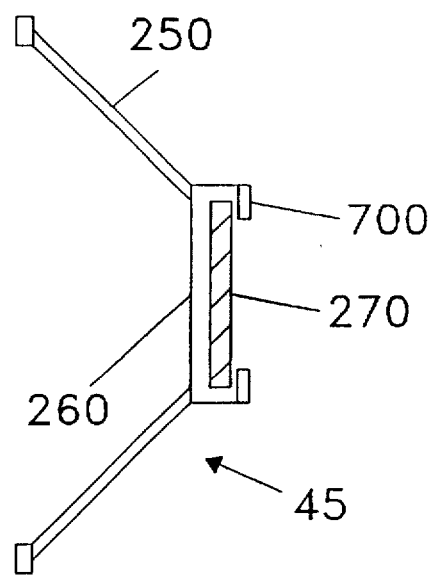
FIG. 7A shows a side view of the calibration device according to yet another embodiment of the invention.
Figure 7B:
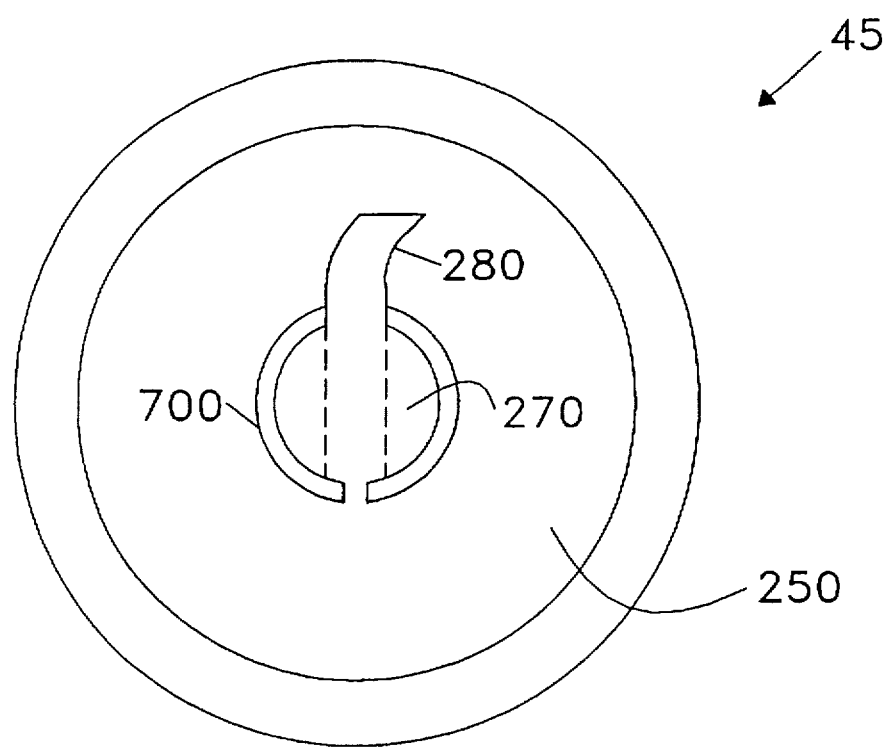
FIG. 7B shows the calibration device as viewed from above.

FIG. 7A shows a side view of calibration device 45 according to yet another embodiment of the invention. Here, calibration target 270 is held in place by ridge 700 alone or together with static cling between target 270 and window 260. Ridge 700 can be part of window 260 or a separate piece. FIG. 7B shows calibration device 45 as viewed from above.

Spectroscopic Measurements

U.S. Pat. No. 5,353,790, the contents of which are incorporated herein by reference, presents a method and apparatus for determining bilirubin concentration in human tissue such as skin. In particular, the patent discusses reflecting light from skin to be tested to determine bilirubin concentration. The approach corrects for maturity-dependent optical properties of the skin including the amount of melanin in the skin and the amount of blood in the skin. Reflected red to infrared light is used to determine the maturity-dependent optical properties, reflected red light is used to determine melanin content, and reflected yellow-orange light is used to determine the amount of blood in the skin. These quantities are used, in combination with reflected blue light, to calculate cutaneous bilirubin concentration.

Spectroscopy System

Figure 8A:
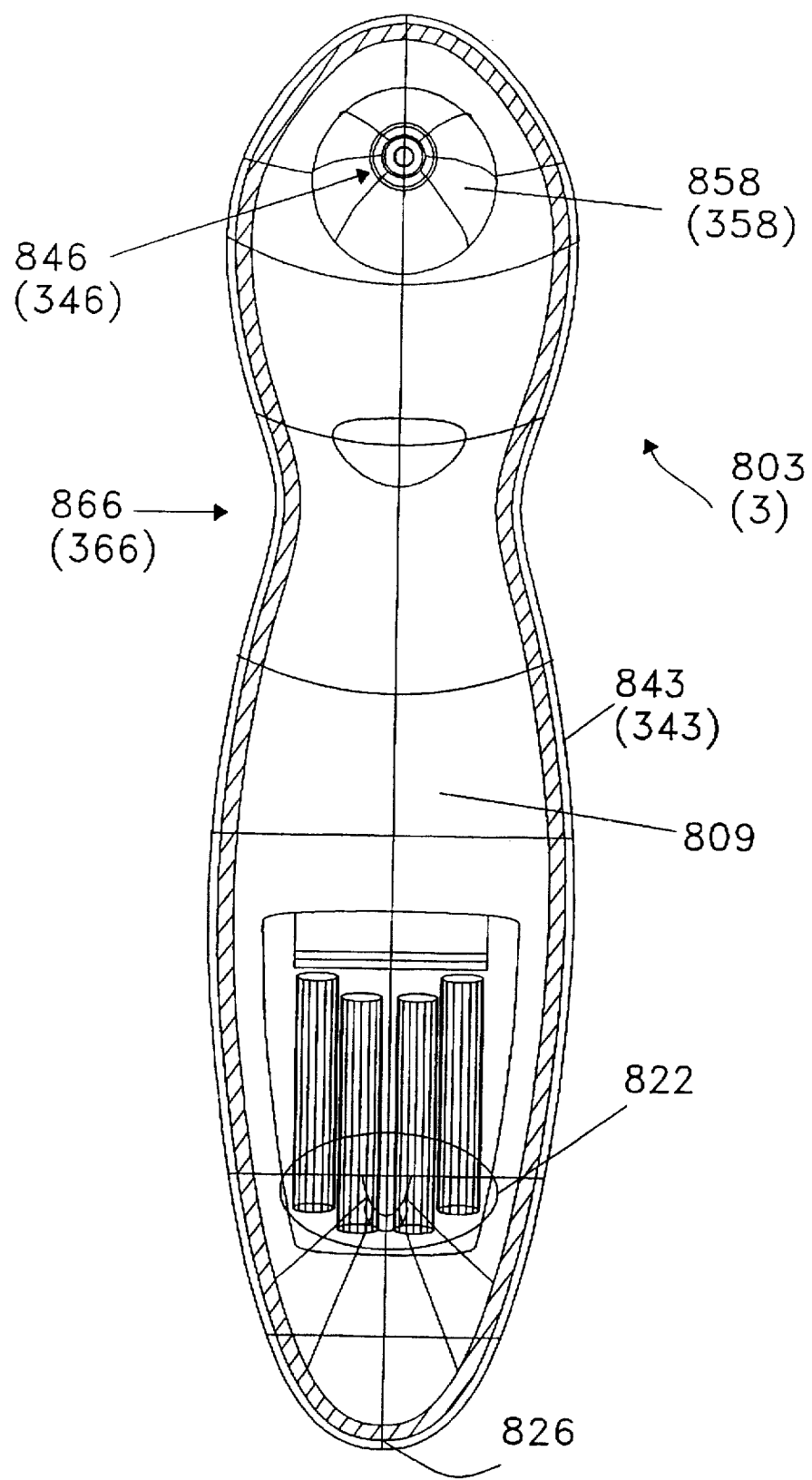
FIGS. 8A, 8B, and 8C show a front, side and back view, respectively, of a spectrometer system.
Figure 8B:
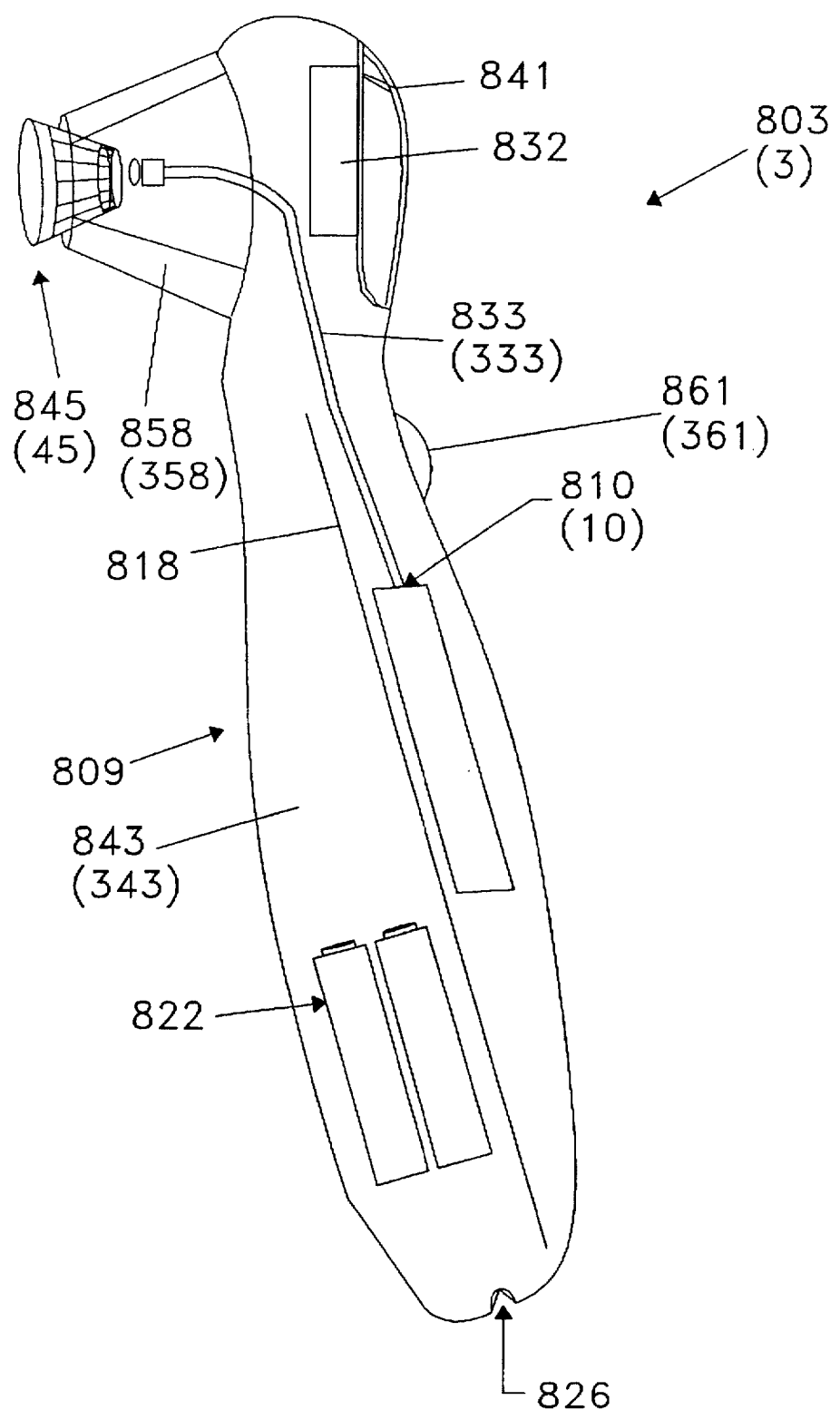
Figure 8C:
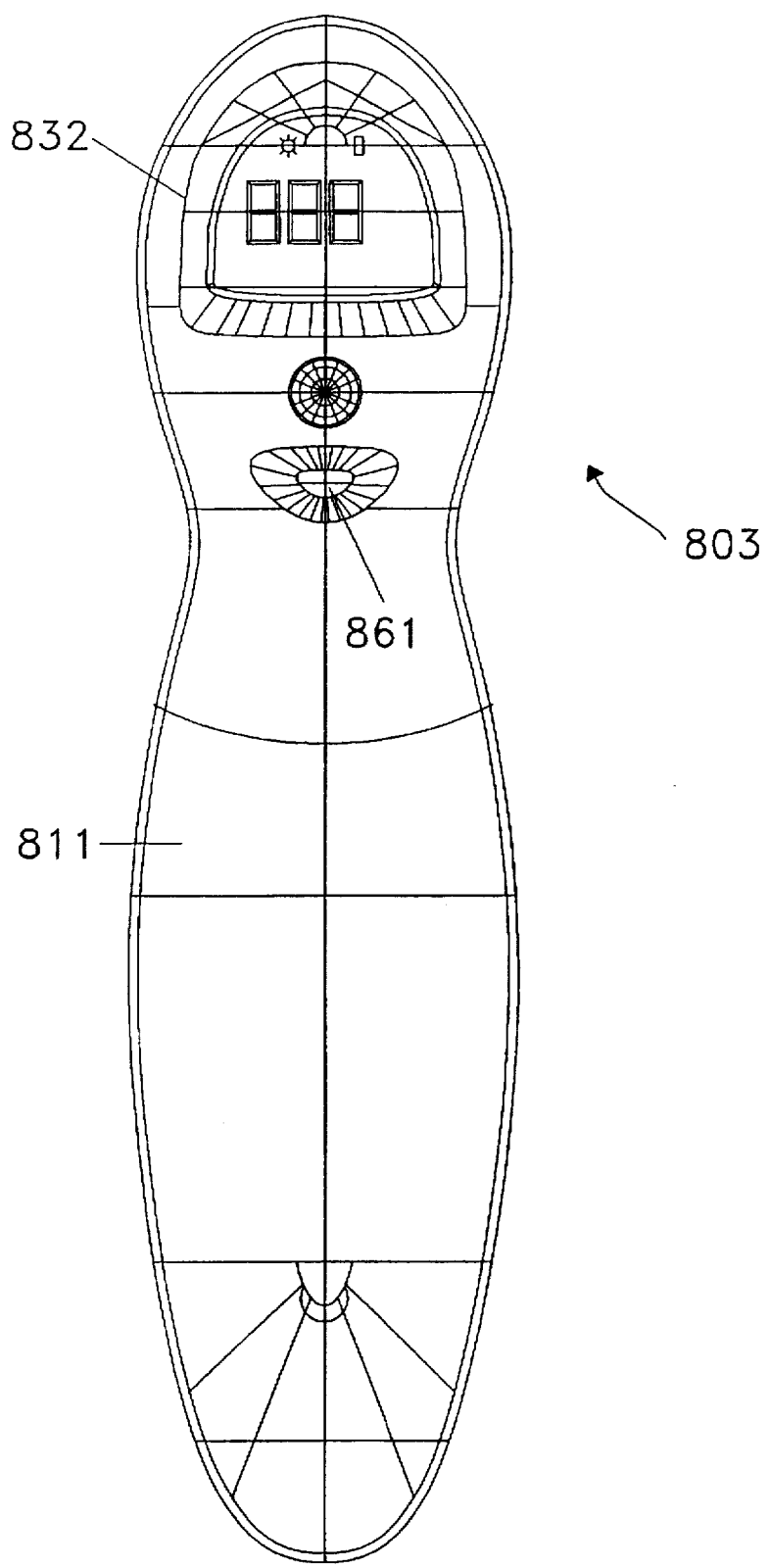
Figure 8D:
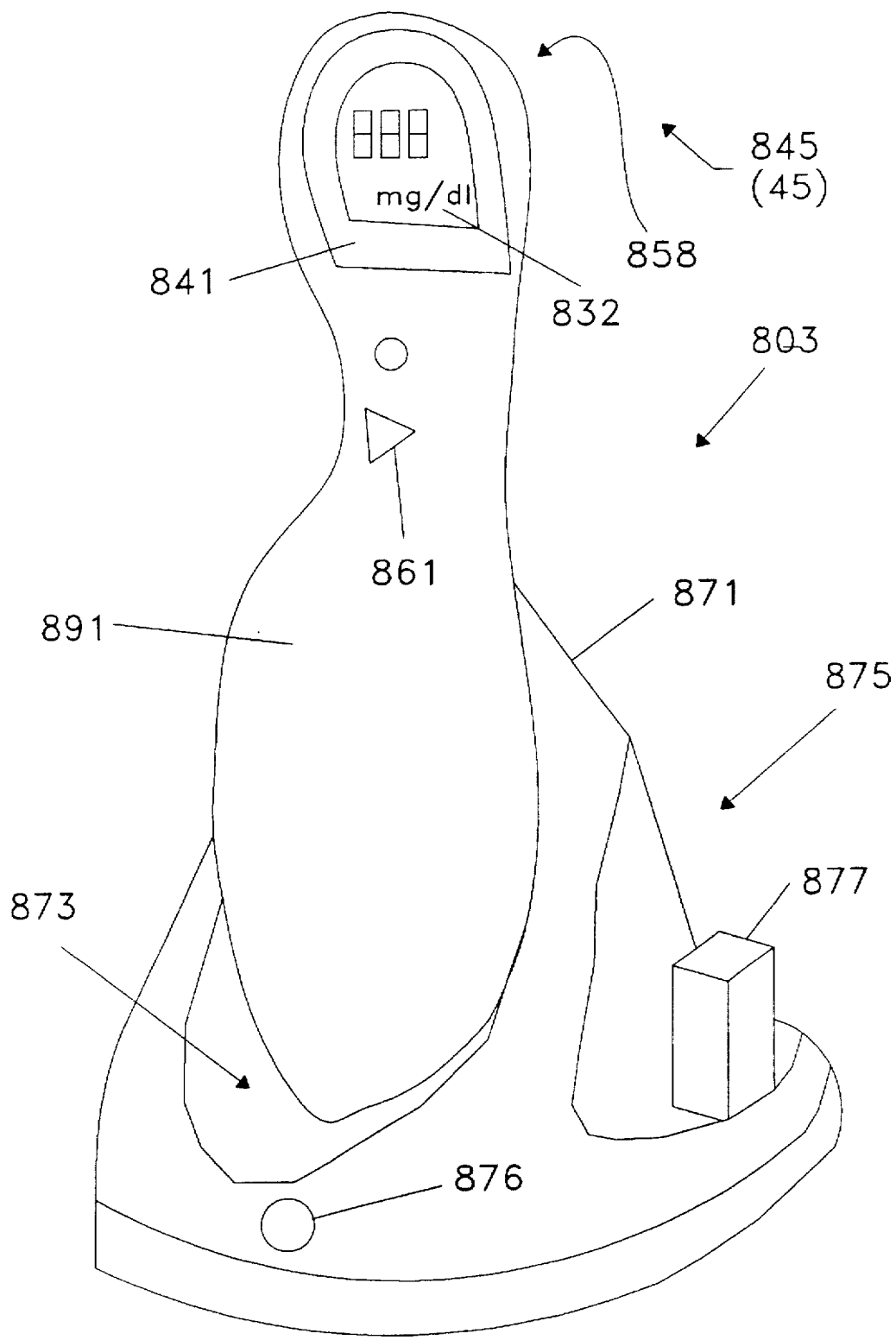
FIG. 8D shows a spectrometer system in a charging stand, according to one embodiment of the invention.

FIGS. 8A, 8B, and 8C show a front, side and back view, respectively, of a spectrometer system 803, and FIG. 8D shows a spectrometer system 803 in a charging stand 871 according to one embodiment of the invention. FIG. 8A shows a front portion 809 of spectroscopic system 803 which utilizes a disposable calibration device 845 (corresponding to the previously discussed disposable calibration device 45) for a spectrometer 810. As will be discussed with reference to FIG. 9B, spectrometer 810 (not shown) can include a microspectrometer such as that offered by American Laubscher Corporation of Farmingdale, N.Y. called the VIS/NIR microspectrometer.

The elements in spectrometer system 803 which have similar counterparts in the previously discussed system 3, will also have the earlier reference numbers indicated in parentheses in FIGS. 8A and 8B. Spectrometer system 803 can operate in the visible, uv and/or infrared regions. Spectrometer system 803 includes a housing 843 which is approximately the size of a human hand. Spectrometer 810 is coupled to calibration device 845 via optical fiber 833 (see FIG. 8B). Calibration device 845 is inserted into an opening end 846 of cone-shaped holder 858 of housing 843. Curved portion 866 of housing 843 allows the hand to comfortably hold spectrometer system 803.

FIG. 8B shows a side view of spectrometer system 803 including spectrometer 810 and push button 861. Spectrometer 810 is mounted on a printed circuit (pc) board 818 which is powered by batteries 822. Batteries 822 can be recharged when placed in a power adapter stand at charger connection 826. A liquid crystal display (LCD) device 832 is also coupled to pc board 818, and LCD device 832 displays measurement results, instructions, warnings, etc. at viewing area 841. Spectrometer 810 is controlled by a processor (see FIGS. 9A and 9B) also mounted on pc board 818.

FIG. 8C shows a back view of system 803 which includes back portion 811 and a full view of LCD device 832. A person can initiate a measurement calibration and then a measurement by pressing push button 861 with his or her thumb. In particular, once a calibration measurement has been performed, tear tab 280 (see previous figures) is used to peel calibration target 270 away from window 260, and system 803 is now ready to make a measurement on a patient. LCD device 832 indicates when spectrometer system 803 is ready to make a calibration measurement. LCD device 832 further indicates when the calibration measurement has been completed and system 803 is ready to make an actual measurement, and when system 803 has completed the measurement. LCD device 832 also displays the results of those measurements. LCD device 832 can also display a message or other indicator showing that the particular calibration target 270 has already been used and that no additional measurements can be made until a new calibration measurement is made. This can be achieved by the presence of a limit switch (not shown) at the end of tip 858 which detects the presence of device 45. Once the limit switch is engaged, the calibration is enabled and a measurement counter is initialized to zero. Calibration is then performed. System software increments the counter each time a measurement is made to a predetermined maximum. Once the maximum number of measurements is reached, system software indicates that a calibration is again required, and the measurement counter is again initialized to zero. Should the limit switch be disengaged at any time in the measurement sequence, indicating the removal of the disposable tip, the display indicates that a new calibration sequence must be begun immediately. This prevents an operator from using one calibration target more than once.

FIG. 8D shows spectroscopic system 803 with a charging stand 871 for storing and charging system 803. Charging stand 871 includes a center portion 873 for receiving system 803. Center portion 871 serves as both a stand and a recharging unit. Stand 871 has an electrical cord (not shown) which can be plugged into an outlet. Stand 871 includes an electrical receiving unit which receives charger connection 826 (see FIG. 8B). An indicator light 876 indicates when spectroscopic system 803 is properly placed in center portion 873 so that recharging is taking place. Stand 871 further includes a side receiving portion 875 which can be used to place a supply 877 of calibration devices 845.

Figure 9A:
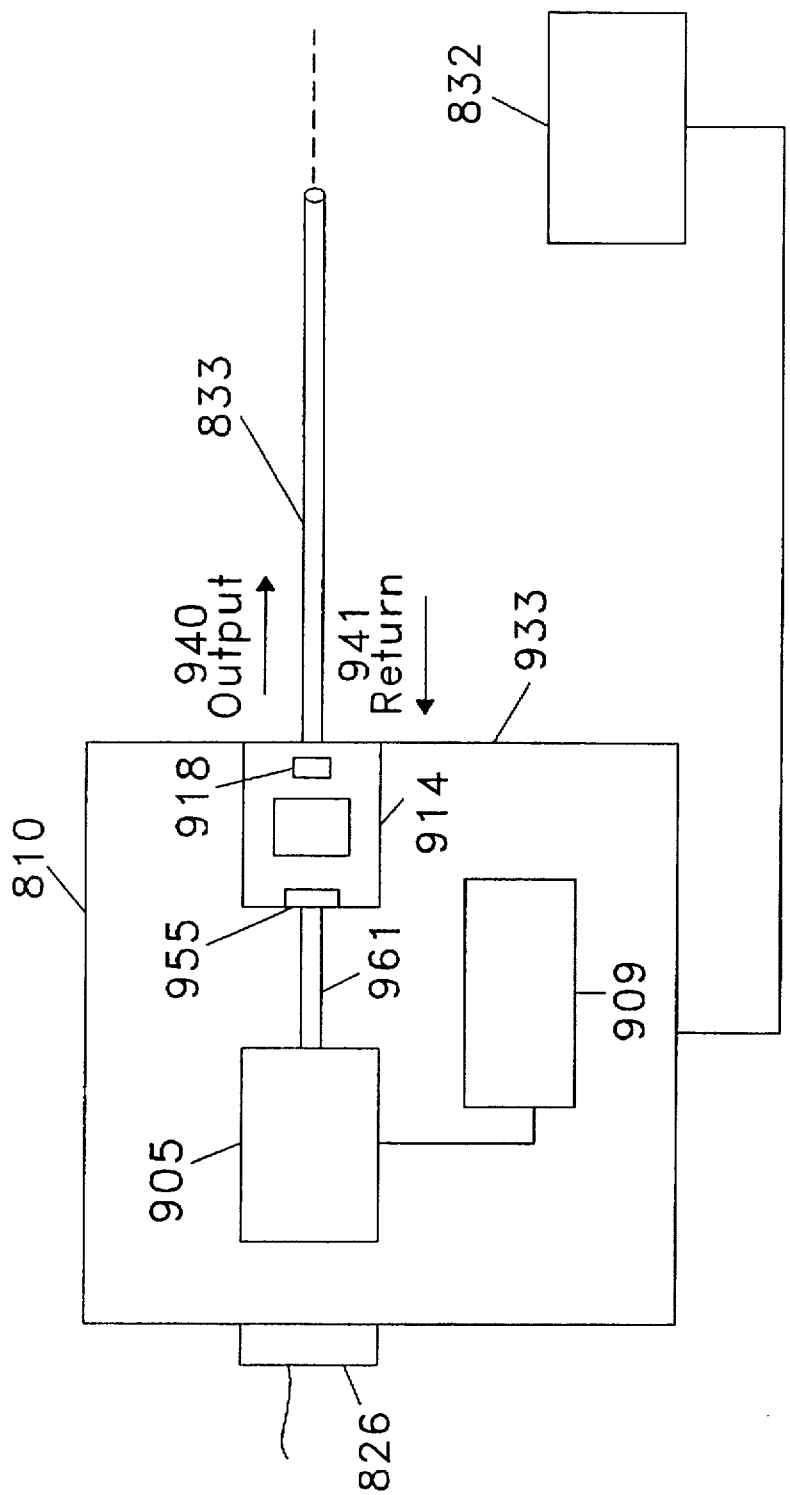
FIG. 9A is a schematic diagram of certain elements of a spectrometer system 803 including a spectrometer instrument.
Figure 9B:
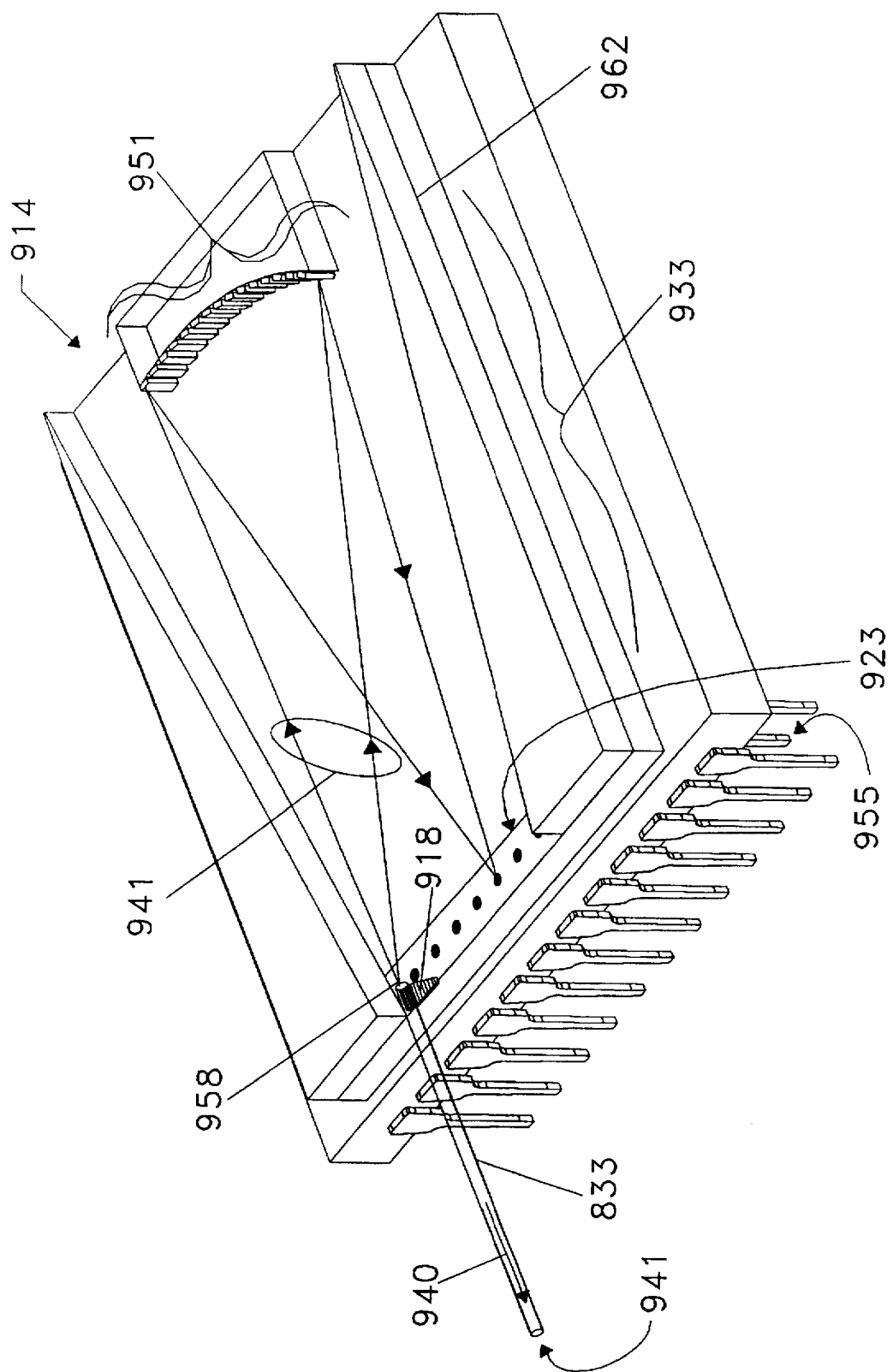
FIG. 9B shows a cut away view of an optical unit in that spectrometer instrument.

FIG. 9A is a schematic diagram of certain elements of system 803, and in particular, of spectrometer instrument 810 which includes an optical unit 914, a central processor unit (cpu) 905, and memory 909. FIG. 9B shows a cut away view of optical unit 914 including an optical source 918, a detector array 923, an optical grating 951 and output 955 which couples optical unit 914 to cpu 905 via bus 961.

Referring to FIG. 9A, spectroscopic instrument 810 includes central processor unit (cpu) 905 and memory unit 909 which controls optical unit 914. Optical unit 914 may include an optical source 918 which may be a tungsten halogen bulb, a noble gas filled tungsten bulb or several LED's covering the desired regions of the optical spectrum. The optical source 918 may also be placed at location 858 in the device housing to illuminate the subject directly, without coupling into a fiber. Output 955 is connected to cpu 905 via bus 961, thereby allowing optical unit 914 to be controlled by cpu 905.

FIG. 9B shows a more detailed view of one embodiment of the invention which utilizes a microspectrometer offered by American Laubscher Corporation of Farmingdale, N.Y. called the VIS/NIR microspectrometer. The cut away view of optical unit 914 shows optical source 918 with detector unit 933 which includes a detector array 923 and a reflection grating 951. Optical radiation 940 is output from optical source 918 and is transmitted via fiber 833 to the material or tissue (not shown) to be measured. The return signal 941 travels back down optical fiber 833 and is output from fiber end 958 into a type of waveguide 962 (cut away) and is incident on reflection grating 951. Reflection grating 951 achieves self-focussing of radiation 941 to different points or detectors on detector array 923 depending on the intensity of wavelengths in radiation 941.

System 803 operates as follows. The following discussion will include reference to FIG. 4A (showing calibration device 45 with calibration target 270), FIG. 8B (showing spectroscopy system 803 and device 45), and FIGS. 9A and 9B (showing spectrometer instrument 810 with optical unit 914). First, calibration target 270 starts out being arranged on window 260 of device 45 and a user pushes button 361 which indicates that radiation 940 is output to calibration target 270. Calibration target 270 has a known spectral characteristic. The actual return radiation 941 results in a detected intensity at individual detectors on detector array 923, thereby yielding a measured calibration characteristic. This measured calibration characteristic is compared to the expected or known spectral characteristic of calibration target 270 and a resulting adjustment value (which could be an array of values) is determined. Calibration target 270 is then removed and a measurement of tissue or material 40 is made by outputting radiation 940 as above. A resulting spectral characteristic is then output from detector array 923 which in turn is adjusted by cpu 905 using the adjustment value or characteristic to yield a calibrated spectral characteristic. The calibrated spectral characteristic can then be used to determine some measurable characteristic of material 40. One such measurement is a nonintrusive bilirubin measurement according to one embodiment of the invention as will now be discussed.

Bilirubin Measurement Process

Bilirubin can be measured in the aqueous of the eye based on the fluorescent signature. Bilirubin can also be directly measured in the sclera (white) of the eye based on the fluorescent signature. Reflectance measurements can also be made on the tympanic membrane of the ear. Finally, reflectance/scattering based measurements can be made on the skin.

Current literature has indicted that the aqueous levels are likely to yield the same results as serum levels of albumin bound bilirubin. However, measurements on five jaundiced adults showed very low signal levels. Direct measurements in the aqueous are also difficult due to low signal levels. This is probably due to the photoconversion taking place in that location, i.e., too much light is allowed into the aqueous in a typical person. There are also difficulties in the evaluation of human factors (such as the fact that infants may not stare in a particular direction for an extended period of time) for an infant measurement. Consequently, direct measurement in the aqueous is not preferred due to the low signal-to-noise ratio and poor human factors.

Direct measurements in the sclera is advantageous in that the yellow color is clearly visible and hence the presence of bilirubin is obvious. Also, this approach is advantageous over a skin based measurement, because it avoids the issue of variations in skin color or thickness. The approach was tested on five jaundiced adults. The approach yielded good signal levels unlike the measurements in the aqueous. However, repeatability was not very good. Also, data indicated a type of photobleaching effect from the excitation light, even during the data collection interval, spatial distribution was also not constant due among other things to eyelid shading. Finally, measurements on subjects shifted dramatically after those subjects spent some time outside compared to the measurements before those subjects went outside. Consequently, direct measurement in the sclera although yielding a high signal-to-noise, is not very repeatable and encounters poor human factors.

Direct measurements on the tympanic membrane suffers from several shortcomings including poor vascularization, difficulty in determining levels of bilirubin in the membrane, poor human factors, particularly on premature babies.

Reflectance/scattering cutaneous measurements seem to be the most promising non-invasive approach to measuring bilirubin. Also, cutaneous measurements provide a simple interface with which to work.

U.S. Pat. No. 5,353,790 shows a technique which makes it possible to separate different constituents. That patent discusses the absorption spectrum of melanin and shows that melanin absorption essentially decreases linearly with increasing wavelength in the visible region. Moreover, since the melanin absorption varies orders of magnitudes over the visible regime, variations in the pigmentation will cause large absolute changes in the absorption at the shorter wavelengths, but the same magnitude changes will cause relatively minuscule absolute changes in the very long wavelengths (>800 nm). The melanin pigmentation measured in the far red wavelength range (650-750 nm) was found to have a pivot point at around 837 nm.

Spectroscopic system 803 takes advantage of the above phenomena and uses spectral reflectance to determine a serum bilirubin level in mg/dL (milligrams of bilirubin per deciliters of blood) as will now be discussed.

Figure 10:
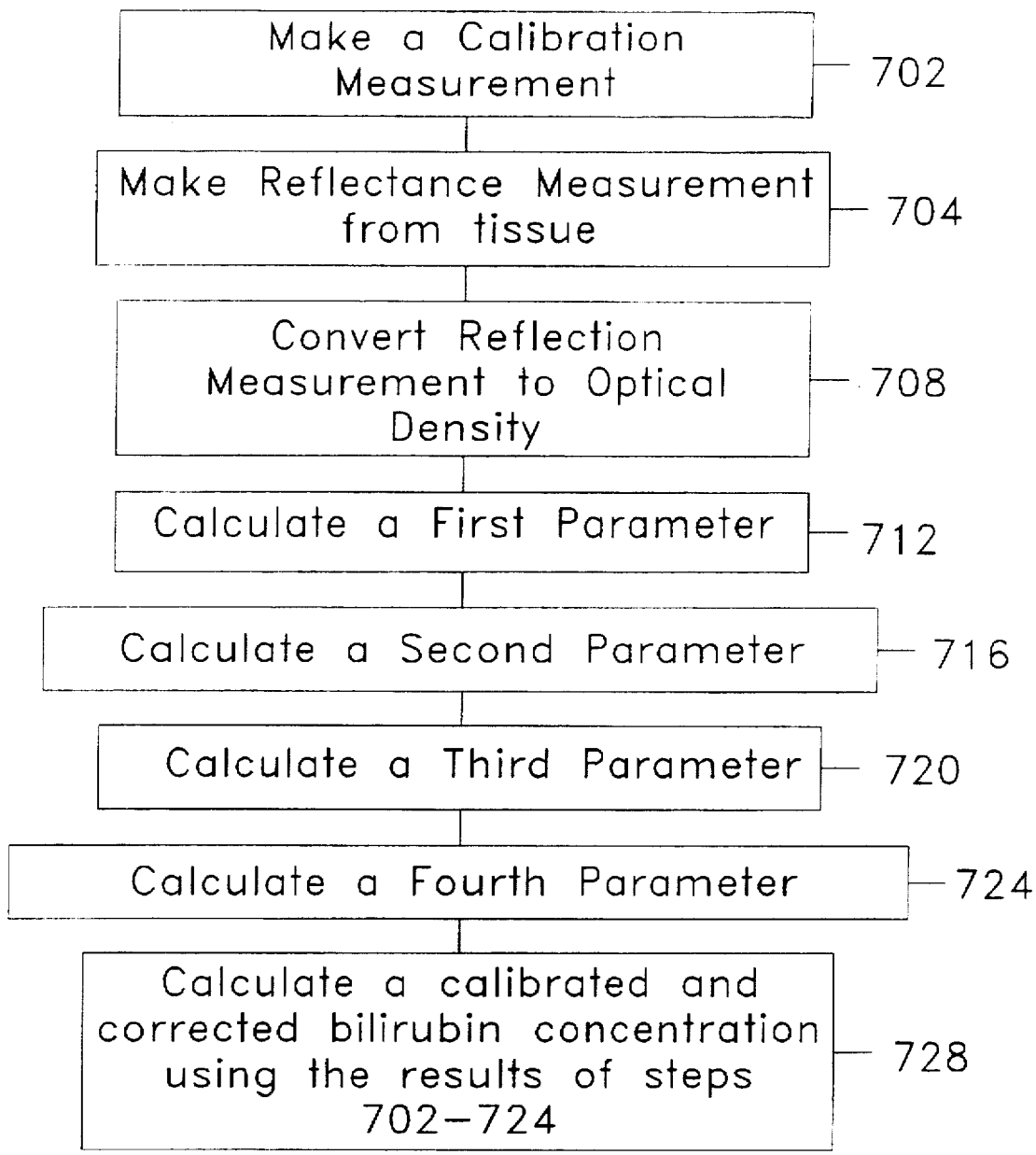
FIG. 10 shows how spectroscopic system performs bilirubin measurements on a patient.

FIG. 10 shows how spectroscopic system 803 performs bilirubin measurements on a patient. The steps performed are an improved approach of that which is discussed in U.S. Pat. No. 5,353,790 by Jacques et al., the contents of which are incorporated herein by reference. Step 702 involves performing a calibration measurement in a manner similar to that described in FIG. 3E. This involves simply outputting radiation to the calibration target, measuring the return signal (due to reflection where reflection is meant to include any type of scattering) to yield a measured calibration spectrum or calibration data which is compared to an expected calibration spectrum which is known a priori depending on the material on surface 41 (see, for example, FIGS. 2A or 3A). Also, the difference between the expected or known spectrum and the measured spectrum can serve as the calibration data which can be used to modify actual measured data, thereby compensating for unit to unit and time varying changes in source luminosity, delivery optics, collection optics, detection sensitivity, electronic drift, and environmental conditions such as temperature and humidity. The processor on PC board 818 (see FIGS. 8A-8C) can perform the above comparison. Alternatively, part or all of the comparison can be performed with specifically designed digital and/or analog hardware.

Step 704 involves making a reflection measurement (which includes scattering) of the tissue by illuminating the tissue with light and detecting a frequency spectrum of light reflected from said tissue. Step 708 involves converting the reflection (scattering) measurement from step 702 into optical density. Step 712 then involves calculating from a first portion of the spectrum, a first parameter indicative of a maturity of the tissue. Step 716 involves calculating from a second portion of the spectrum, a second parameter indicative of an amount of melanin in the tissue. Step 720 involves calculating from a third portion of the spectrum, a third parameter indicative of a blood content of the tissue. Step 724 involves calculating from a fourth portion of the spectrum, a fourth parameter indicative of an uncorrected bilirubin concentration in the tissue. Step 728 involves calculating a corrected bilirubin concentration in the tissue as a function of the first, second, third and fourth parameters.

Figure 11:
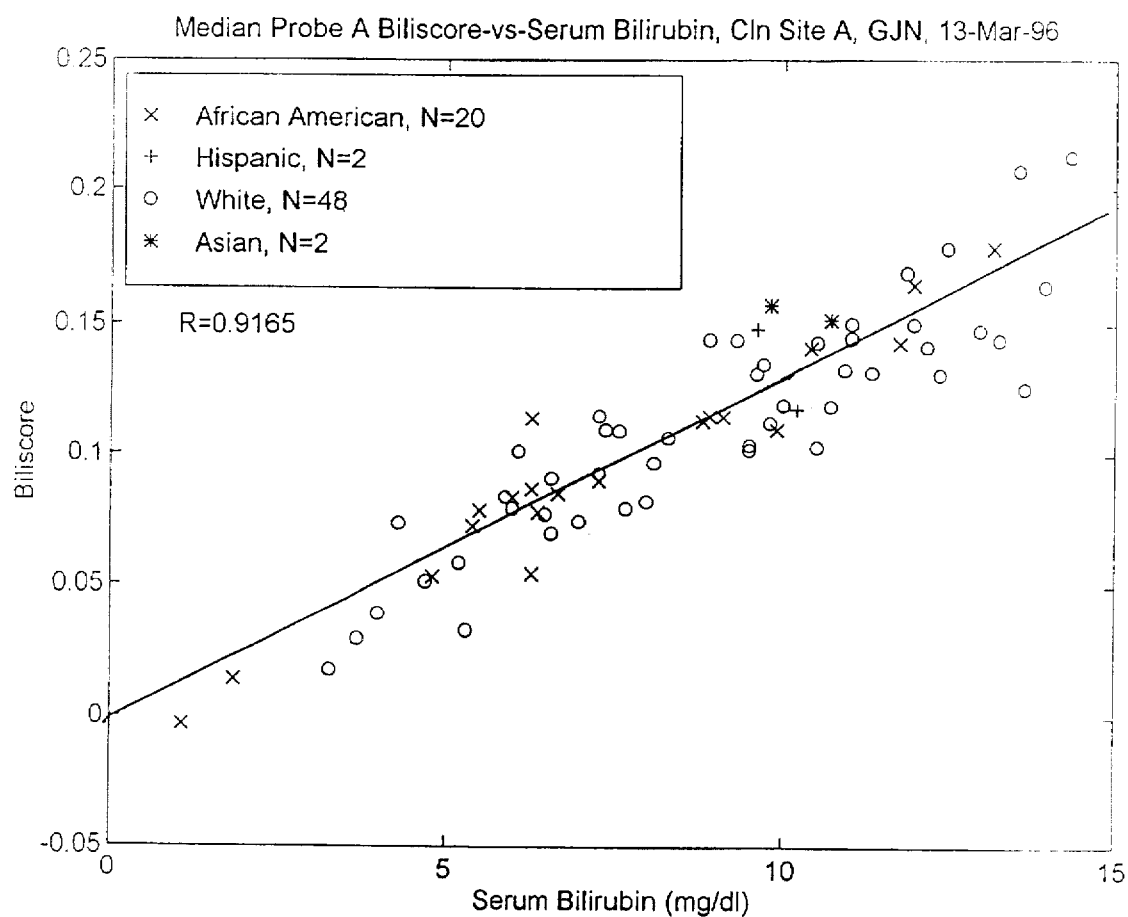
FIG. 11 shows the results of data taken using the method of FIG. 10 versus a standard serum bilirubin (heel stick) method.

FIG. 11 shows the results of data taken using the method of FIG. 10 versus a standard serum bilirubin (heel stick) method. The subjects were 72 full term babies of varied ethnic background, with 20 African Americans, 2 Hispanic Americans, 48 white Americans, and 2 Asian Americans. "R" represents the correlation coefficient between the measurement method described in FIG. 10, versus the standard method of serum bilirubin. The correlation coefficient shown is 0.9165 with a perfect correlation given as 1.0000. The tests represent a purely prospective application of the process of FIG. 10.

Numerous and additional modifications and variations of the present invention are possible in light of the above teachings. It is therefore to be understood that within the scope of the appended claims, the invention may be practiced otherwise than specifically claimed.

What is claimed is:

1. A spectrometer system, comprising:
   - a spectrometer instrument which transmits radiation to a material or tissue in order to effect measurements;
   - a calibration device holder on the spectrometer instrument;
   - a calibration device which can be attached to said calibration device holder, said calibration device comprising:
     - a structure including an opening through which the radiation can be transmitted; and
     - a removable calibration target arranged on said opening, said removable calibration target for returning a portion of said radiation for calibrating the spectrometer instrument, wherein the removable calibration target is to be removed from said opening while said structure remains attached to said calibration device holder to allow a measurement to be made on the material or tissue.

2. The spectrometer system as claimed in claim 1, further comprising a window arranged at said opening.

3. The spectrometer system as claimed in claim 2, wherein said removable calibration target includes a tear tab which can be gripped to remove said removable calibration target from said window.

4. The spectrometer system as claimed in claim 2, wherein said structure and said window comprises a barrier between the material or tissue and the spectrometer system.

5. The spectrometer system as claimed in claim 2, wherein said structure and said window comprise an infection shield between the material or tissue and the spectrometer system.

6. The spectrometer system as claimed in claim 2, further comprising a tab attached to said calibration target, wherein said calibration target comprises a perforation which causes said calibration target to become mechanically altered when said calibration target is pulled away from said window using said tab.

7. The spectrometer system as claimed in claim 2, further comprising a first tab and a second tab, wherein said calibration target comprises a perforation which divides said calibration target into first and second regions and said first and second tabs are attached to said first and second regions, respectively.

8. The spectrometer system as claimed in claim 2, further comprising a landing attachment, said landing attachment comprising an extension of said window.

9. The spectrometer system as claimed in claim 1, wherein said removable calibration target includes a tear tab which can be gripped to remove said removable calibration target from said opening.

10. The spectrometer system as claimed in claim 1, wherein said structure is shaped to provide separation between the material or tissue and the spectrometer system.

11. The spectrometer system as claimed in claim 1, wherein said spectrometer instrument comprises:

an optical unit for outputting output radiation and for receiving received radiation and detecting said received radiation as spectral return information; and a processor coupled to said optical unit for receiving and processing said spectral return information.

12. The spectrometer system as claimed in claim 11, wherein said optical unit comprises an optical source for outputting said output radiation, and a detector array for detecting said received radiation and outputting said spectral return information.

13. The spectrometer system as claimed in claim 12, wherein said optical unit further comprises a grating for diffracting said return radiation according to wavelengths therein toward said detector array.

14. The spectrometer system as claimed in claim 1, wherein said structure of said calibration device is readily removable from said spectrometer system.

15. The spectrometer system as claimed in claim 1, further comprising a landing attachment attached to said structure.

16. The spectrometer system as claimed in claim 15, wherein said landing attachment further comprises a landing annulus.

17. The spectrometer system as claimed in claim 1, wherein said structure comprises a ridge arranged along said opening said ridge maintaining said removable calibration target at the opening of said structure.

18. A spectrometer system, comprising:

a spectrometer instrument which transmits radiation to a material or tissue in order to effect measurements;

a calibration device holder on said spectrometer instrument;

a calibration device which can be attached to said calibration device holder, said calibration device comprising:

a structure through which the radiation can be transmitted; and a removable calibration target arranged about said structure and capable of returning a portion of said radiation for calibrating the spectrometer instrument, wherein the removable calibration target is to be removed from said structure while said structure remains attached to said calibration device holder to allow a measurement to be made on the material or tissue.

19. A spectrometer system, comprising:

a housing including a calibration device holder;

a spectrometer instrument arranged in said housing, said spectrometer instrument transmitting radiation through said calibration device holder to a material or tissue in order to effect measurements; and a calibration device which can be attached to said calibration device holder, said calibration device comprising:

a structure including a window through which the radiation can be transmitted and a removable calibration target arranged on said window and capable of returning a portion of said radiation for calibrating the spectrometer instrument, wherein the removable calibration target is to be removed from said window while the structure remains attached to the calibration device holder to allow a measurement to be made on the material or tissue.

20. A method for calibrating a spectrometer system that outputs radiation from an output end, comprising the steps of:

placing a calibration device over the output end of the spectrometer system, wherein the calibration device has a removable calibration target;

activating the spectrometer system to perform a calibration measurement wherein radiation is reflected from the calibration target back toward the output end of the spectrometer system and wherein the reflected radiation is received by the output end of the spectrometer system; and removing the removable calibration target from the calibration device.

21. The method as claimed in claim 20, wherein said removing step comprises removing the removable calibration target from the calibration device while leaving a window attached to the spectrometer system, and said radiation is output through the window.

22. The method as claimed in claim 20, further comprising the step of calculating calibration information based on the calibration measurement.

23. A method for transcutaneous determination of bilirubin concentration in tissue, comprising the steps of:

performing a calibration measurement on a calibration target and storing resulting calibration data;

illuminating said tissue with light;

detecting a frequency spectrum of light scattered from said tissue;

calculating, from a first portion of said spectrum, a first parameter indicative of a maturity of said tissue;

calculating, from a second portion of said spectrum, a second parameter indicative of an amount of melanin in said tissue;

calculating, from a third portion of said spectrum, a third parameter indicative of a blood content of said tissue;

calculating, from a fourth portion of said spectrum, a fourth parameter indicative of an uncorrected bilirubin concentration in said tissue;

calculating a corrected bilirubin concentration in said tissue as a function of said first, second, third, and fourth parameter;

adjusting said corrected bilirubin concentration using said resulting calibration data to yield a calibrated and corrected bilirubin concentration, whereby said calibrated and corrected bilirubin concentration may compensate for any or all of the following: unit to unit and time varying changes in source luminosity, delivery optics, collection optics, detection sensitivity, electronic drift, and environmental conditions such as temperature and humidity.

24. A method for transcutaneous determination of bilirubin concentration in tissue, comprising the steps of:

arranging a calibration device on a spectrometer system, wherein said calibration device comprises a calibration target;

performing a calibration measurement on a calibration target and storing resulting calibration data;

removing the calibration target from the calibration device;

illuminating said tissue with light;

detecting a frequency spectrum of light reflected from said tissue;

calculating, from a first portion of said spectrum, a first parameter indicative of a maturity of said tissue;

calculating, from a second portion of said spectrum, a second parameter indicative of an amount of melanin in said tissue;

calculating, from a third portion of said spectrum, a third parameter indicative of a blood content of said tissue;

calculating, from a fourth portion of said spectrum, a fourth parameter indicative of an uncorrected bilirubin concentration in said tissue;

calculating a calibrated and corrected bilirubin concentration in said tissue as a function of said first, second, third, and fourth parameter along with said resulting calibration data.

25. A spectrometer system, comprising:

a spectrometer instrument which transmits radiation from an output end to a material or tissue in order to effect measurements; and a calibration device including a removable calibration target, said calibration device being removably arranged on the instrument to scatter said radiation as calibration radiation, wherein a portion of the calibration radiation returns to the output end of the instrument, and wherein said spectrometer instrument uses the returned portion of the calibration radiation to effect calibration, whereby said spectrometer can effect a subsequent calibrated measurement of the material upon removal of said removable calibration target.

26. The spectrometer system as claimed in claim 25, wherein said calibration device comprises a structure including an opening through which the radiation can be transmitted.

27. The spectrometer system as claimed in claim 26, wherein said calibration device further comprises a removable calibration target arranged on said opening which scatters said radiation as said calibration radiation.

28. The system of claim 26, wherein the structure of the calibration device remains attached to the instrument during a subsequent calibrated measurement.

29. A spectrometer system, comprising:

a spectrometer instrument which transmits light to a material or tissue in order to effect measurement;

a calibration device holder;

a calibration device which can be arranged in said calibration device holder, said calibration device comprising:

a structure including an opening, said opening having a window arranged thereat, wherein the light transmitted from the spectrometer instrument can pass through said window thereby illuminating the material or tissue, and said window allows the transmission of light scattered or reflected from the material or tissue illuminated; and a removable calibration target arranged on said opening and capable of returning a portion of the light transmitted from the spectrometer instrument for calibrating the spectrometer instrument.

30. The spectrometer instrument as claimed in claim 29, wherein a frequency spectrum can be detected from the light scattered or reflected from the material or tissue.

31. A method for calibrating a spectrometer system that outputs radiation from an output end, comprising the steps of:

placing a calibration device on the output end of the spectrometer system, wherein the calibration device has a window and a removable calibration target arranged on said window;

activating the spectrometer system to perform a calibration measurement; and removing the removable calibration target from the calibration device while leaving the window on the spectrometer system such that radiation passes through the window during subsequent measurements.

32. A spectrometer system, comprising:

a spectrometer instrument which transmits radiation to a material or tissue in order to effect measurements;

a calibration device holder;

a calibration device which can be arranged in said calibration device holder, said calibration device comprising:

a structure including an opening through which the radiation can be transmitted, and a removable calibration target arranged on said opening, said removable calibration target including a user graspable tear tab for removing the calibration target from the opening, wherein the calibration target is to be removed from said opening to allow a measurement to be made on the material or tissue.

33. The system of claim 32, wherein said removable calibration target further comprises a perforation which causes the calibration target to become mechanically altered when the calibration target is removed from the window.

34. The system of claim 32, wherein the user graspable tear tab comprises a first tab and a second tab, wherein the perforation divides the calibration target into first and second regions, and wherein the first and second tabs are attached to the first and second regions, respectively.

\* \* \* \* \*